United States Patent
Nagaki et al.

(10) Patent No.: US 9,073,846 B2
(45) Date of Patent: *Jul. 7, 2015

(54) INTEGRATED PROCESS FOR THE PRODUCTION OF ACRYLIC ACIDS AND ACRYLATES

(71) Applicant: Celanese International Corporation, Irving, CA (US)

(72) Inventors: Dick Nagaki, The Woodlands, TX (US); Craig J. Peterson, Houston, TX (US); Josefina T. Chapman, Houston, TX (US); Sean Mueller, Pasadena, TX (US); Himanshu Lodha, Houston, TX (US)

(73) Assignee: Celanese International Corporation, Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/910,180

(22) Filed: Jun. 5, 2013

(65) Prior Publication Data

US 2014/0364644 A1    Dec. 11, 2014

(51) Int. Cl.
  *C07C 67/00*   (2006.01)
  *C07C 51/353*  (2006.01)
  *C07C 67/347*  (2006.01)

(52) U.S. Cl.
  CPC .............. *C07C 51/353* (2013.01); *C07C 67/347* (2013.01)

(58) Field of Classification Search
  CPC ........................................................ C07C 67/00
  USPC ........................................................ 560/211
  See application file for complete search history.

(56) References Cited

U.S. PATENT DOCUMENTS

| | | |
|---|---|---|
| 3,538,122 A | 11/1970 | Friedrichsen et al. |
| 3,541,143 A | 11/1970 | Nakano et al. |
| 4,276,197 A | 6/1981 | Vartuli et al. |
| 4,866,194 A | 9/1989 | Glaeser et al. |
| 4,892,856 A | 1/1990 | Kawajiri et al. |
| 4,994,608 A | 2/1991 | Torrence et al. |
| 5,001,259 A | 3/1991 | Smith et al. |
| 5,026,908 A | 6/1991 | Smith et al. |
| 5,144,068 A | 9/1992 | Smith et al. |
| 5,364,824 A | 11/1994 | Andrews et al. |
| 5,504,247 A | 4/1996 | Saxer et al. |
| 5,523,480 A | 6/1996 | Bauer, Jr. et al. |
| RE35,377 E | 11/1996 | Steinberg et al. |
| 5,599,976 A | 2/1997 | Scates et al. |
| 5,821,111 A | 10/1998 | Gaddy et al. |
| 6,143,930 A | 11/2000 | Singh et al. |
| 6,232,352 B1 | 5/2001 | Vidalin et al. |
| 6,509,180 B1 | 1/2003 | Verser et al. |
| 6,544,924 B1 | 4/2003 | Jackson et al. |
| 6,627,770 B1 | 9/2003 | Cheung et al. |
| 6,657,078 B2 | 12/2003 | Scates et al. |
| 6,685,754 B2 | 2/2004 | Kindig et al. |
| 6,852,881 B2 | 2/2005 | De Decker et al. |
| 7,005,541 B2 | 2/2006 | Cheung et al. |
| 7,053,147 B2 | 5/2006 | Jackson et al. |
| 7,115,772 B2 | 10/2006 | Picard et al. |
| 7,208,624 B2 | 4/2007 | Scates et al. |
| 7,300,555 B2 | 11/2007 | Schroeder et al. |
| 7,351,559 B2 | 4/2008 | Verser et al. |
| 7,507,562 B2 | 3/2009 | Verser et al. |
| 7,601,865 B2 | 10/2009 | Verser et al. |
| 7,682,812 B2 | 3/2010 | Verser et al. |
| 7,803,969 B2 | 9/2010 | Nordhoff et al. |
| 7,842,844 B2 | 11/2010 | Atkins |
| 7,851,397 B2 | 12/2010 | Liang et al. |
| 7,884,253 B2 | 2/2011 | Stites et al. |
| 7,888,082 B2 | 2/2011 | Verser et al. |
| 8,299,132 B2 | 10/2012 | Gracey et al. |
| 8,299,133 B2 | 10/2012 | Gracey et al. |
| 8,329,960 B2 | 12/2012 | Gracey et al. |
| 8,378,153 B2 | 2/2013 | Daniel et al. |
| 2003/0233012 A1 | 12/2003 | Jackson et al. |
| 2005/0261522 A1 | 11/2005 | Isaguliants et al. |
| 2008/0193989 A1 | 8/2008 | Verser et al. |
| 2009/0048354 A1 | 2/2009 | Bell et al. |
| 2009/0170963 A1 | 7/2009 | Atkins |

(Continued)

FOREIGN PATENT DOCUMENTS

| | | |
|---|---|---|
| DE | 2145049 | 3/1973 |
| EP | 1904426 | 4/2008 |

(Continued)

OTHER PUBLICATIONS

U.S. Appl. No. 14/139,856, filed Jan. 8, 2014, Nagaki et al.*
International Search Report and Written Opinion for PCT/US2014/040204 mailed Sep. 12, 2014.
M. Ai., Applied Catalysis, 36, pp. 221-230 (1988).
M. Ai., Applied Catalysis, 48, pp. 51-61 (1989).
M. Ai., Applied Catalysis, 54, 1989, pp. 29-36.
M. Ai., Applied Catalysis, 252, 2003, pp. 185-191.
M. Ai., Journal of Catalysis, 107, 1987, pp. 201-208.

(Continued)

*Primary Examiner* — Yong Chu
*Assistant Examiner* — Sonya Wright

(57) ABSTRACT

A process for producing a crude product stream including an acrylate product and an alkylenating agent and separating at least a portion of the crude product stream to form alkylenating agent and intermediate product streams. The alkylenating agent stream comprises at least 1 wt % alkylenating agent and the intermediate product stream comprises acrylate products in high concentration. The crude product stream is formed by contacting acetic acid and formaldehyde in the presence of at least one aldol condensation catalyst under conditions effective to form the stream. Catalysts which are particularly useful are multielement oxide active materials of the general formula

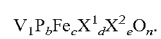

$V_1 P_b Fe_c X^1_d X^2_e O_n$.

20 Claims, 3 Drawing Sheets

(56) References Cited

U.S. PATENT DOCUMENTS

| | | |
|---|---|---|
| 2009/0246111 A1 | 10/2009 | Kato et al. |
| 2009/0281354 A1 | 11/2009 | Mariansky et al. |
| 2009/0292148 A1 | 11/2009 | Gracey et al. |
| 2010/0016454 A1 | 1/2010 | Gracey et al. |
| 2011/0071311 A1 | 3/2011 | Johnson et al. |
| 2011/0224462 A1 | 9/2011 | Ditzel et al. |
| 2012/0071687 A1 | 3/2012 | Herzog et al. |
| 2012/0071688 A1 | 3/2012 | Herzog et al. |

FOREIGN PATENT DOCUMENTS

| | | |
|---|---|---|
| EP | 1967507 | 9/2008 |
| EP | 2060553 | 5/2009 |
| EP | 2072486 | 6/2009 |
| EP | 2072487 | 6/2009 |
| EP | 2072488 | 6/2009 |
| EP | 2072490 | 6/2009 |
| EP | 2072492 | 6/2009 |

OTHER PUBLICATIONS

M. Ai., Journal of Catalysis, 124, 1990, pp. 293-296.
M. Ai., Shokubai, 29, 522 (1987), www.shokubai.org/jnl/cgi-bin/ccotw.cgi.
Brinker C J & Scherer G W, "Sol-Gel Science" published by Academic Press (1990).
Iler R K, The Chemistry of Silica, (Wiley, New York, 1979).
Jubb & Bowen, Journal of Material Science, vol. 22, pp. 1963-1970 (1987).
Monros, et al., Journal of Material Science, vol. 28, p. 5832 (1993).

* cited by examiner

INTEGRATED PROCESS FOR THE PRODUCTION OF ACRYLIC ACIDS AND ACRYLATES

FIELD OF THE INVENTION

The present invention relates generally to the production of acrylic acid. More specifically, the present invention relates to the production of crude acrylic acid via the condensation of acetic acid and formaldehyde and the subsequent purification thereof.

BACKGROUND OF THE INVENTION

α,β-unsaturated acids, particularly acrylic acid and methacrylic acid, and the ester derivatives thereof are useful organic compounds in the chemical industry. These acids and esters are known to readily polymerize or co-polymerize to form homopolymers or copolymers. Often the polymerized acids are useful in applications such as superabsorbents, dispersants, flocculants, and thickeners. The polymerized ester derivatives are used in coatings (including latex paints), textiles, adhesives, plastics, fibers, and synthetic resins.

Because acrylic acid and its esters have long been valued commercially, many methods of production have been developed. One exemplary acrylic acid ester production process utilizes: (1) the reaction of acetylene with water and carbon monoxide; and/or (2) the reaction of an alcohol and carbon monoxide, in the presence of an acid, e.g., hydrochloric acid, and nickel tetracarbonyl, to yield a crude product comprising the acrylate ester as well as hydrogen and nickel chloride. Another conventional process involves the reaction of ketene (often obtained by the pyrolysis of acetone or acetic acid) with formaldehyde, which yields a crude product comprising acrylic acid and either water (when acetic acid is used as a pyrolysis reactant) or methane (when acetone is used as a pyrolysis reactant). These processes have become obsolete for economic, environmental, or other reasons.

More recent acrylic acid production processes have relied on the gas phase oxidation of propylene, via acrolein, to form acrylic acid. The reaction can be carried out in single- or two-step processes but the latter is favored because of higher yields. The oxidation of propylene produces acrolein, acrylic acid, acetaldehyde and carbon oxides. Acrylic acid from the primary oxidation can be recovered while the acrolein is fed to a second step to yield the crude acrylic acid product, which comprises acrylic acid, water, small amounts of acetic acid, as well as impurities such as furfural, acrolein, and propionic acid. Purification of the crude product may be carried out by azeotropic distillation. Although this process may show some improvement over earlier processes, this process suffers from production and/or separation inefficiencies. In addition, this oxidation reaction is highly exothermic and, as such, creates an explosion risk. As a result, more expensive reactor design and metallurgy are required. Also, the cost of propylene is often prohibitive.

US Patent Publication No. 2012/0071688 discloses a process for preparing acrylic acid from methanol and acetic acid in which the methanol is partially oxidized to formaldehyde in a heterogeneously catalyzed gas phase reaction. The product gas mixture thus obtained and an acetic acid source are used to obtain a reaction gas input mixture that comprises acetic acid and formaldehyde. The acetic acid is used in excess over the formaldehyde. The formaldehyde present in reaction gas input mixture is aldol-condensed with the acetic acid via heterogeneous catalysis to form acrylic acid. Unconverted acetic acid still present alongside the acrylic acid in the product gas mixture is removed therefrom and is recycled to the reaction gas input mixture.

The aldol condensation reaction of formaldehyde and acetic acid and/or carboxylic acid esters has been disclosed in literature. This reaction forms acrylic acid and is often conducted over a catalyst. For example, condensation catalysts consisting of mixed oxides of vanadium and phosphorus were investigated and described in M. Ai, *J. Catal.*, 107, 201 (1987); M. Ai, *J. Catal.*, 124, 293 (1990); M. Ai, *Appl. Catal.*, 36, 221 (1988); and M. Ai, *Shokubai*, 29, 522 (1987). The acetic acid conversions in these reactions, however, may leave room for improvement. Although this reaction is disclosed, the aldol condensation catalysts disclosed therein can be improved upon in terms of providing high acetic acid conversions and acrylate production yields.

Thus, the need exists for processes for producing purified acrylic acid and, in particular, for processes which utilize improved aldol condensation catalysts capable of providing high acetic acid conversions and acrylate production yields and for processes capable of effectively purifying the crude product thus obtained.

The references mentioned above are hereby incorporated by reference.

BRIEF DESCRIPTION OF DRAWINGS

The invention is described in detail below with reference to the appended drawings, wherein like numerals designate similar parts.

SUMMARY OF THE INVENTION

Figure 1:
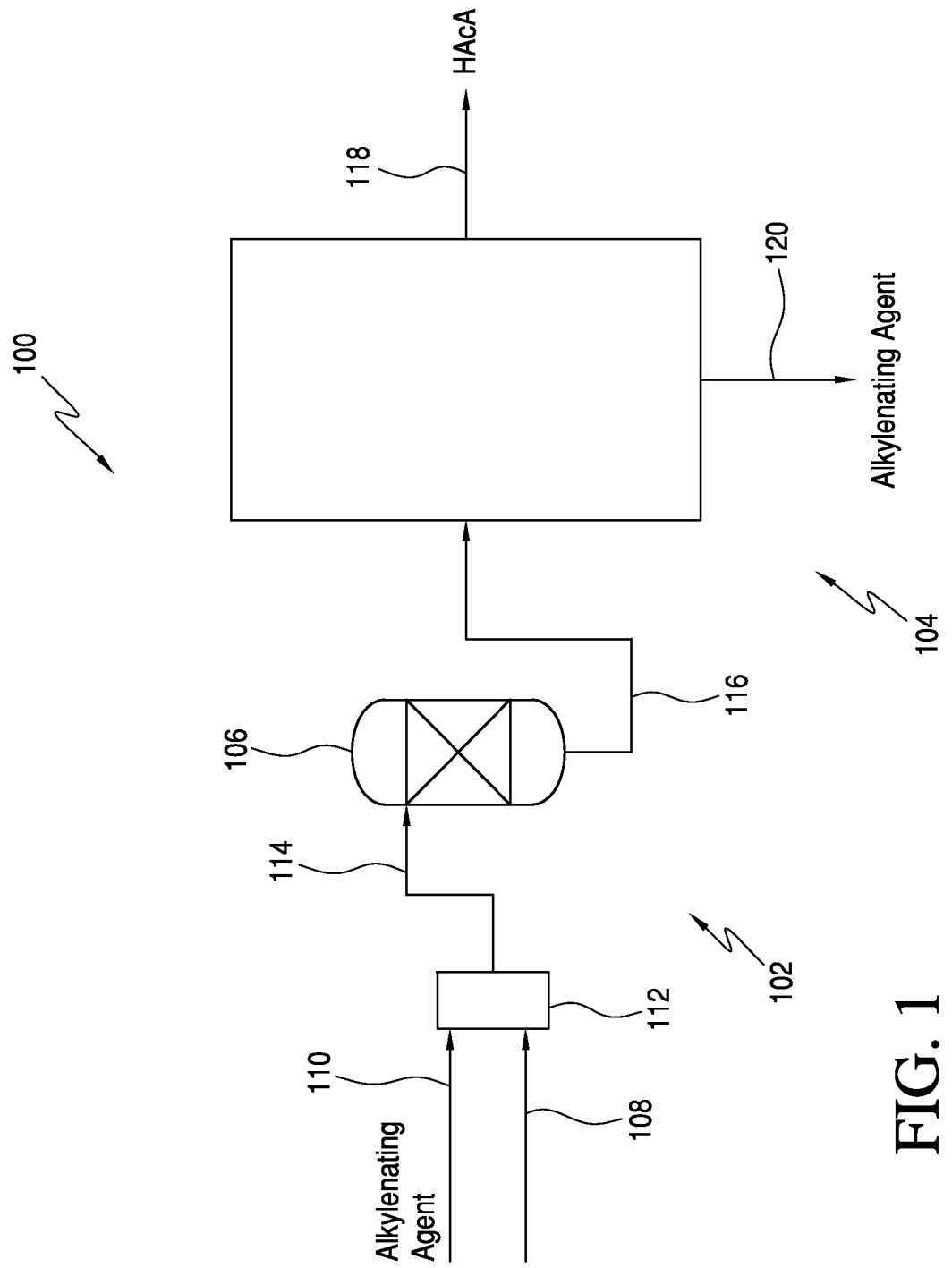
FIG. 1 is a schematic of an acrylic acid reaction/separation system in accordance with an embodiment of the present invention.

In one embodiment, the invention is to a process for producing acrylic acid, methacrylic acid, and/or the salts and esters thereof. Preferably, the inventive process yields an acrylic acid product. The process comprises the step of providing a crude product stream comprising acrylic acid and/or other acrylate products and an alkylenating agent. The crude product stream may comprise at least 1 wt % alkylenating agent. The alkylenating agent may be, for example, formaldehyde. In preferred embodiments, the crude product stream is formed by contacting acetic acid and formaldehyde in the presence of at least one aldol condensation catalyst and under conditions effective to form the crude product stream. In one embodiment, the inventive process further comprises the step of separating at least a portion of the crude product stream to form an alkylenating agent stream and an intermediate acrylic product stream. Preferably, the alkylenating stream comprises at least 1 wt % alkylenating agent and the intermediate acrylic product stream comprises acrylic acid and/or other acrylate products in high concentrations. Aldol condensation catalysts which have been found to be particularly useful are multielement oxide active materials of the general formula I $$V_1P_bFe_cX^1_dX^2_eO_n \qquad (I),$$

in which the variables are each defined as follows:

$X^1$ is Mo, Bi, Co, Ni, Si, Zn, Hf, Zr, Ti, Cr, Mn, Cu, B, Sn and/or Nb, preferably Nb, Mo, Zn and/or Hf, $X^2$ is Li, K, Na, Rb, Cs and/or Tl, b is 0.9 to 2.0, preferably 0.9 to 1.5, more preferably 0.9 to 1.2 and most preferably 1.0 to 1.1, c ranges from 0.01 to 1 d ranges from 0 to 0.1, e ranges from 0 to 0.1, and n is the stoichiometric coefficient of the element oxygen, which is determined by the stoichiometric coefficients of the non-oxygen elements and the charge numbers thereof in II.

DETAILED DESCRIPTION OF THE INVENTION

Introduction

Production of unsaturated carboxylic acids such as acrylic acid and methacrylic acid and the ester derivatives thereof via most conventional processes have been limited by economic and environmental constraints. In the interest of finding a new reaction path, the aldol condensation reaction of acetic acid and an alkylenating agent, e.g., formaldehyde, has been investigated. This reaction may yield a unique crude product that comprises, inter alia, a higher amount of (residual) formaldehyde, which is generally known to add unpredictability and problems to separation schemes. Although there may be some disclosure relating to the aldol condensation reaction, there is little if any disclosure relating to suitable separation schemes for handling the separation of the high formaldehyde content crude products. Other conventional reactions, e.g., propylene oxidation or ketene/formaldehyde, do not yield crude products that comprises higher amounts of formaldehyde. The primary reactions and the side reactions in propylene oxidation do not create formaldehyde. In the reaction of ketene and formaldehyde, a two-step reaction is employed and the formaldehyde is confined to the first stage. Also, the ketene is highly reactive and converts substantially all of the reactant formaldehyde. As a result of these features, very little, if any, formaldehyde remains in the crude product exiting the reaction zone. Because no formaldehyde is present in crude products formed by these conventional reactions, the separation schemes associated therewith have not addressed the problems and unpredictability that accompany crude products that have higher formaldehyde content.

Even though the aldol condensation reaction of acetic acid and formaldehyde is known, the aldol condensation catalysts that are disclosed can be improved upon in terms of providing high acetic acid conversions and acrylate production yields.

In one embodiment, the present invention is to a process for producing acrylic acid, methacrylic acid, and/or the salts and esters thereof. As used herein, acrylic acid, methacrylic acid, and/or the salts and esters thereof, collectively or individually, may be referred to as "acrylate products." The use of the terms acrylic acid, methacrylic acid, or the salts and esters thereof, individually, does not exclude the other acrylate products, and the use of the term acrylate product does not require the presence of acrylic acid, methacrylic acid, and the salts and esters thereof.

The inventive process, in one embodiment, includes the step of providing a crude product stream comprising the acrylic acid and/or other acrylate products. The crude product stream of the present invention, unlike most conventional acrylic acid-containing crude products, further comprises a significant portion of at least one alkylenating agent. Preferably, the at least one alkylenating agent is formaldehyde. For example, the crude product stream may comprise at least 0.5 wt % alkylenating agent(s), e.g., at least 1 wt %, at least 5 wt %, at least 7 wt %, at least 10 wt %, or at least 25 wt %. In terms of ranges, the crude product stream may comprise from 0.5 wt % to 50 wt % alkylenating agent(s), e.g., from 1 wt % to 45 wt %, from 1 wt % to 25 wt %, from 1 wt % to 10 wt %, or from 5 wt % to 10 wt %. In terms of upper limits, the crude product stream may comprise less than 50 wt % alkylenating agent(s), e.g., less than 45 wt %, less than 25 wt %, or less than 10 wt %.

In one embodiment, the crude product stream of the present invention further comprises water. For example, the crude product stream may comprise less than 60 wt % water, e.g., less than 50 wt %, less than 40 wt %, or less than 30 wt %. In terms of ranges, the crude product stream may comprise from 1 wt % to 60 wt % water, e.g., from 5 wt % to 50 wt %, from 10 wt % to 40 wt %, or from 15 wt % to 40 wt %. In terms of upper limits, the crude product stream may comprise at least 1 wt % water, e.g., at least 5 wt %, at least 10 wt %, or at least 15 wt %.

In one embodiment, the crude product stream of the present invention comprises very little, if any, of the impurities found in most conventional acrylic acid crude product streams. For example, the crude product stream of the present invention may comprise less than 1000 wppm of such impurities (either as individual components or collectively), e.g., less than 500 wppm, less than 100 wppm, less than 50 wppm, or less than 10 wppm. Exemplary impurities include acetylene, ketene, beta-propiolactone, higher alcohols, e.g., $C_{2+}$, $C_{3+}$, or $C_{4+}$, and combinations thereof. Importantly, the crude product stream of the present invention comprises very little, if any, furfural and/or acrolein. In one embodiment, the crude product stream comprises substantially no furfural and/or acrolein, e.g., no furfural and/or acrolein. In one embodiment, the crude product stream comprises less than less than 500 wppm acrolein, e.g., less than 100 wppm, less than 50 wppm, or less than 10 wppm. In one embodiment, the crude product stream comprises less than less than 500 wppm furfural, e.g., less than 100 wppm, less than 50 wppm, or less than 10 wppm. Furfural and acrolein are known to act as detrimental chain terminators in acrylic acid polymerization reactions. Also, furfural and/or acrolein are known to have adverse effects on the color of purified product and/or to subsequent polymerized products.

In addition to the acrylic acid and the alkylenating agent, the crude product stream may further comprise acetic acid, water, propionic acid, and light ends such as oxygen, nitrogen, carbon monoxide, carbon dioxide, methanol, methyl acetate, methyl acrylate, acetaldehyde, hydrogen, and acetone. Exemplary compositional data for the crude product stream are shown in Table 1. Components other than those listed in Table 1 may also be present in the crude product stream.

TABLE 1

CRUDE ACRYLATE PRODUCT STREAM COMPOSITIONS

| Component | Conc. (wt %) | Conc. (wt %) | Conc. (wt %) | Conc. (wt %) |
|---|---|---|---|---|
| Acrylic Acid | 1 to 75 | 1 to 50 | 5 to 50 | 10 to 40 |
| Alkylenating Agent(s) | 0.5 to 50 | 1 to 45 | 1 to 25 | 1 to 10 |
| Acetic Acid | 1 to 90 | 1 to 70 | 5 to 50 | 10 to 50 |
| Water | 1 to 60 | 5 to 50 | 10 to 40 | 15 to 40 |
| Propionic Acid | 0.01 to 10 | 0.1 to 10 | 0.1 to 5 | 0.1 to 1 |
| Oxygen | 0.01 to 10 | 0.1 to 10 | 0.1 to 5 | 0.1 to 1 |
| Nitrogen | 0.1 to 20 | 0.1 to 10 | 0.5 to 5 | 0.5 to 4 |
| Carbon Monoxide | 0.01 to 10 | 0.1 to 10 | 0.1 to 5 | 0.5 to 3 |
| Carbon Dioxide | 0.01 to 10 | 0.1 to 10 | 0.1 to 5 | 0.5 to 3 |
| Other Light Ends | 0.01 to 10 | 0.1 to 10 | 0.1 to 5 | 0.5 to 3 |

The unique crude product stream of the present invention may be separated in a separation zone to form a final product, e.g., a final acrylic acid product. As noted above, the high content of alkylating agent in the crude product creates problems and unpredictability in separation schemes. The configurations of the separation schemes of the present invention surprisingly and unexpectedly, are capable of effectively separating the high alkylating agent content streams to yield a suitable purified acrylate product. In one embodiment, the inventive process comprises the step of separating at least a portion of the crude product stream to form an alkylating agent stream and an intermediate product stream. This separating step may be referred to as an "alkylating agent split." In one embodiment, the alkylating agent stream comprises significant amounts of alkylating agent(s). For example, the alkylating agent stream may comprise at least 1 wt % alkylating agent(s), e.g., at least 5 wt %, at least 10 wt %, at least 15 wt %, or at least 25 wt %. In terms of ranges, the alkylating stream may comprise from 1 wt % to 75 wt % alkylating agent(s), e.g., from 3 to 50 wt %, from 3 wt % to 25 wt %, or from 10 wt % to 20 wt %. In terms of upper limits, the alkylating stream may comprise less than 75 wt % alkylating agent(s), e.g. less than 50 wt % or less than 40 wt %. In preferred embodiments, the alkylating agent is formaldehyde.

As noted above, the presence of alkylating agent in the crude product stream adds unpredictability and problems to separation schemes. Without being bound by theory, it is believed that formaldehyde reacts in many side reactions with water to form by-products. The following side reactions are exemplary.

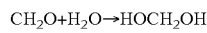

$$CH_2O + H_2O \rightarrow HOCH_2OH$$

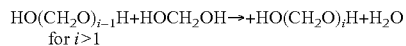

$$HO(CH_2O)_{i-1}H + HOCH_2OH \rightarrow HO(CH_2O)_iH + H_2O$$
for $i > 1$

Without being bound by theory, it is believed that, in some embodiments, as a result of these reactions, the alkylating agent, e.g., formaldehyde, acts as a "light" component at higher temperatures and as a "heavy" component at lower temperatures. The reaction(s) are exothermic. Accordingly, the equilibrium constant increases as temperature decreases and decreases as temperature increases. At lower temperatures, the larger equilibrium constant favors methylene glycol and oligomer production and formaldehyde becomes limited, and, as such, behaves as a heavy component. At higher temperatures, the smaller equilibrium constant favors formaldehyde production and methylene glycol becomes limited. As such, formaldehyde behaves as a light component. In view of these difficulties, as well as others, the separation of streams that comprise water and formaldehyde cannot be expected to behave as a typical two-component system. These features contribute to the unpredictability and difficulty of the separation of the unique crude product stream of the present invention.

The present invention, surprisingly and unexpectedly, achieves effective separation of alkylating agent(s) from the inventive crude product stream to yield a purified product comprising acrylate product and very low amounts of other impurities. It has now been discovered that by first removing a good portion of the alkylating agent from the condensation product gas mixture, the efficiency of the remaining separations are made more efficient. Without being bound by theory, it is believed that the removal of alkylating agent early in the separation process lessens the separation burden on the remaining separation units. Without removing the alkylating agent, e.g., formaldehyde, in accordance with the present invention, each additional separation unit would be burdened with separation of residual formaldehyde, which is known to be difficult. The separation schemes of some of the references, in contrast to the embodiments of the present invention, focus on separation of acrylic acid, acetic acid, and inert diluent. The difficult separation of alkylating agent, e.g., formaldehyde, is not discussed in detail. Without being bound by theory, it is believed that the performance of the alkylating agent split as discussed herein provides for effective separation of additional components elsewhere in the separation scheme.

In one embodiment, the alkylating split is performed such that a lower amount of acetic acid is present in the resulting alkylating stream. Preferably, the alkylating agent stream comprises little or no acetic acid. As an example, the alkylating agent stream, in some embodiments, comprises less than 50 wt % acetic acid, e.g., less than 45 wt %, less than 25 wt %, less than 10 wt %, less than 5 wt %, less than 3 wt %, or less than 1 wt %. Surprisingly and unexpectedly, the present invention provides for the lower amounts of acetic acid in the alkylating agent stream, which, beneficially reduces or eliminates the need for further treatment of the alkylating agent stream to remove acetic acid. In some embodiments, the alkylating agent stream may be treated to remove water therefrom, e.g., to purge water.

In some embodiments, the alkylating agent split is performed in at least one column, e.g., at least two columns or at least three columns. Preferably, the alkylating agent is performed in a two column system. In other embodiments, the alkylating agent split is performed via contact with an extraction agent. In other embodiments, the alkylating agent split is performed via precipitation methods, e.g., crystallization, and/or azeotropic distillation. Of course, other suitable separation methods may be employed either alone or in combination with the methods mentioned herein.

Without being bound by theory, it is believed that alkylating agents, e.g., formaldehyde, may not be sufficiently volatile at lower pressures. Thus, maintenance of the separation unit pressures, e.g., column pressures, at low levels surprisingly and unexpectedly provides for efficient separation operations. In addition, it has surprisingly and unexpectedly been found that maintenance of these low pressures may inhibit and/or eliminate polymerization of the acrylate products, e.g., acrylic acid, which may contribute to fouling of the column(s). Also, it has surprisingly and unexpectedly been found that by maintaining the temperature of the units, e.g., columns, at a low level (as discussed below), may inhibit and/or eliminate polymerization of the acrylate products.

The intermediate product stream comprises acrylate products. In one embodiment, the intermediate product stream comprises a significant portion of acrylate products, e.g., acrylic acid. For example, the intermediate product stream may comprise at least 5 wt % acrylate products, e.g., at least 25 wt %, at least 40 wt %, at least 50 wt %, or at least 60 wt %. In terms of ranges, the intermediate product stream may comprise from 5 wt % to 99 wt % acrylate products, e.g. from 10 wt % to 90 wt %, from 25 wt % to 75 wt %, or from 35 wt % to 65 wt %. The intermediate product stream, in one embodiment, comprises little if any alkylating agent. For example, the intermediate product stream may comprise less than 1 wt % alkylating agent, e.g., less than 0.1 wt % alkylating agent, less than 0.05 wt %, or less than 0.01 wt %. In addition to the acrylate products, the intermediate product stream optionally comprises acetic acid, water, propionic acid and other components.

In some cases, the intermediate acrylate product stream comprises higher amounts of alkylating agent. For example, in one embodiment, the intermediate acrylate product stream comprises from 1 wt % to 50 wt % alkylating agent, e.g., from 1 wt % to 10 wt % or from 5 wt % to 50 wt %. In terms of limits, the intermediate acrylate product stream may comprise at least 1 wt % alkylenating agent, e.g., at least 5 wt % or at least 10 wt %.

In one embodiment, the crude product stream is optionally treated, e.g. separated, prior to the separation of alkylenating agent therefrom. In such cases, the treatment(s) occur before the alkylenating agent split is performed. In other embodiments, at least a portion of the intermediate acrylate product stream may be further treated after the alkylenating agent split. As one example, the crude product stream may be treated to remove light ends therefrom. This treatment may occur either before or after the alkylenating agent split, preferably before the alkylenating agent split. In some of these cases, the further treatment of the intermediate acrylate product stream may result in derivative streams that may be considered to be additional purified acrylate product streams. In other embodiments, the further treatment of the intermediate acrylate product stream results in at least one finished acrylate product stream.

In one embodiment, the inventive process operates at a high process efficiency. For example, the process efficiency may be at least 10%, e.g., at least 20% or at least 35%. In one embodiment, the process efficiency is calculated based on the flows of reactants into the reaction zone. The process efficiency may be calculated by the following formula.

Process Efficiency=$2N_{HAcA}/[N_{HOAc}+N_{HCHO}+N_{H2O}]$ where:

$N_{HAcA}$ is the molar production rate of acrylate products; and $N_{HOAc}$, $N_{HCHO}$, and $N_{H2O}$ are the molar feed rates of acetic acid, formaldehyde, and water.

Production of Acrylate Products

Any suitable reaction and/or separation scheme may be employed to form the crude product stream as long as the reaction provides the crude product stream components that are discussed above. For example, in some embodiments, the acrylate product stream is formed by contacting an alkanoic acid, e.g., acetic acid, or an ester thereof with an alkylenating agent, e.g., a methylenating agent, for example formaldehyde, under conditions effective to form the crude acrylate product stream. Preferably, the contacting is performed over a suitable catalyst. The crude product stream may be the reaction product of the alkanoic acid-alkylenating agent reaction. In a preferred embodiment, the crude product stream is the reaction product of the aldol condensation reaction of acetic acid and formaldehyde, which is conducted over a catalyst comprising multielement oxide active materials of the general formula I, as described hereinbefore.

In one embodiment, the crude product stream is the product of a reaction in which methanol with acetic acid are combined to generate formaldehyde in situ. The aldol condensation then follows. In one embodiment, a methanol-formaldehyde solution is reacted with acetic acid to form the crude product stream.

The alkanoic acid, or an ester of the alkanoic acid, may be of the formula R'—$CH_2$—COOR, where R and R' are each, independently, hydrogen or a saturated or unsaturated alkyl or aryl group. As an example, R and R' may be a lower alkyl group containing for example 1-4 carbon atoms. In one embodiment, an alkanoic acid anhydride may be used as the source of the alkanoic acid. In one embodiment, the reaction is conducted in the presence of an alcohol, preferably the alcohol that corresponds to the desired ester, e.g., methanol. In addition to reactions used in the production of acrylic acid, the inventive catalyst, in other embodiments, may be employed to catalyze other reactions.

The alkanoic acid, e.g., acetic acid, may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. As petroleum and natural gas prices fluctuate, becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syngas") that is derived from any available carbon source. U.S. Pat. No. 6,232,352, which is hereby incorporated by reference, for example, teaches a method of retrofitting a methanol plant for the manufacture of acetic acid. By retrofitting a methanol plant, the large capital costs associated with carbon monoxide generation for a new acetic acid plant are significantly reduced or largely eliminated. All or part of the syn gas is diverted from the methanol synthesis loop and supplied to a separator unit to recover carbon monoxide and hydrogen, which are then used to produce acetic acid.

In some embodiments, at least some of the raw materials for the above-described aldol condensation process may be derived partially or entirely from syngas. For example, the acetic acid may be formed from methanol and carbon monoxide, both of which may be derived from syngas. For example, the methanol may be formed by steam reforming syngas, and the carbon monoxide may be separated from syngas. In other embodiments, the methanol may be formed in a carbon monoxide unit, e.g., as described in EP2076480; EP1923380; EP2072490; EP1914219; EP1904426; EP2072487; EO2072492; EP2072486; EP2060553; EP1741692; EP1907344; EP2060555; EP2186787; EP2072488; and U.S. Pat. No. 7,842,844, which are hereby incorporated by reference. Of course, this listing of methanol sources is merely exemplary and is not meant to be limiting. In addition, the above-identified methanol sources, inter alia, may be used to form the formaldehyde, e.g., in situ, which, in turn may be reacted with the acetic acid to form the acrylic acid. The syngas, in turn, may be derived from variety of carbon sources. The carbon source, for example, may be selected from the group consisting of natural gas, oil, petroleum, coal, biomass, and combinations thereof.

Methanol carbonylation processes suitable for production of acetic acid are described in U.S. Pat. Nos. 7,208,624, 7,115,772, 7,005,541, 6,657,078, 6,627,770, 6,143,930, 5,599,976, 5,144,068, 5,026,908, 5,001,259, and 4,994,608, all of which are hereby incorporated by reference.

U.S. Pat. No. RE 35,377, which is hereby incorporated by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form syn gas. The syn gas is converted to methanol which may be carbonylated to acetic acid. U.S. Pat. No. 5,821,111, which discloses a process for converting waste biomass through gasification into syn gas, as well as U.S. Pat. No. 6,685,754 are hereby incorporated by reference.

In one optional embodiment, the acetic acid that is utilized in the condensation reaction comprises acetic acid and may also comprise other carboxylic acids, e.g., propionic acid, esters, and anhydrides, as well as acetaldehyde and acetone.

In one embodiment, the acetic acid fed to the condensation reaction comprises propionic acid. For example, the acetic acid fed to the reaction may comprise from 0.001 wt % to 15 wt % propionic acid, e.g., from 0.001 wt % to 0.11 wt %, from 0.125 wt % to 12.5 wt %, from 1.25 wt % to 11.25 wt %, or from 3.75 wt % to 8.75 wt %. Thus, the acetic acid feed stream may be a cruder acetic acid feed stream, e.g., a less-refined acetic acid feed stream.

As used herein, "alkylenating agent" means an aldehyde or precursor to an aldehyde suitable for reacting with the alkanoic acid, e.g., acetic acid, to form an unsaturated acid, e.g., acrylic acid, or an alkyl acrylate. In preferred embodiments, the alkylenating agent comprises a methylenating agent such as formaldehyde, which preferably is capable of adding a methylene group ($=CH_2$) to the organic acid. Other alkylenating agents may include, for example, acetaldehyde, propanal, butanal, aryl aldehydes, benzyl aldehydes, alcohols, and combinations thereof. This listing is not exclusive and is not meant to limit the scope of the invention. In one embodiment, an alcohol may serve as a source of the alkylenating agent. For example, the alcohol may be reacted in situ to form the alkylenating agent, e.g., the aldehyde.

The alkylenating agent, e.g., formaldehyde, may be derived from any suitable source. Exemplary sources may include, for example, aqueous formaldehyde solutions, anhydrous formaldehyde derived from a formaldehyde drying procedure, trioxane, diether of methylene glycol, and paraformaldehyde. In a preferred embodiment, the formaldehyde is produced via a methanol oxidation process, which reacts methanol and oxygen to yield the formaldehyde.

In other embodiments, the alkylenating agent is a compound that is a source of formaldehyde. Where forms of formaldehyde that are not as freely or weakly complexed are used, the formaldehyde will form in situ in the condensation reactor or in a separate reactor prior to the condensation reactor. Thus for example, trioxane may be decomposed over an inert material or in an empty tube at temperatures over 350° C. or over an acid catalyst at over 100° C. to form the formaldehyde.

In one embodiment, the alkylenating agent corresponds to Formula I.

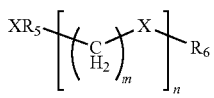

In this formula, $R_5$ and $R_6$ may be independently selected from $C_1$-$C_{12}$ hydrocarbons, preferably, $C_1$-$C_{12}$ alkyl, alkenyl or aryl, or hydrogen. Preferably, $R_5$ and $R_6$ are independently $C_1$-$C_6$ alkyl or hydrogen, with methyl and/or hydrogen being most preferred. X may be either oxygen or sulfur, preferably oxygen; and n is an integer from 1 to 10, preferably 1 to 3. In some embodiments, m is 1 or 2, preferably 1.

In one embodiment, the compound of formula I may be the product of an equilibrium reaction between formaldehyde and methanol in the presence of water. In such a case, the compound of formula I may be a suitable formaldehyde source. In one embodiment, the formaldehyde source includes any equilibrium composition. Examples of formaldehyde sources include but are not restricted to methylal (1,1dimethoxymethane); polyoxymethylenes —($CH_2$—O)$_i$— wherein i is from 1 to 100; formalin; and other equilibrium compositions such as a mixture of formaldehyde, methanol, and methyl propionate. In one embodiment, the source of formaldehyde is selected from the group consisting of 1,1 dimethoxymethane; higher formals of formaldehyde and methanol; and $CH_3$—O—($CH_2$—O)$_i$—$CH_3$ where i is 2.

The alkylenating agent may be used with or without an organic or inorganic solvent.

The term "formalin," refers to a mixture of formaldehyde, methanol, and water. In one embodiment, formalin comprises from 25 wt % to 65% formaldehyde; from 0.01 wt % to 25 wt % methanol; and from 25 wt % to 70 wt % water. In cases where a mixture of formaldehyde, methanol, and methyl propionate is used, the mixture comprises less than 10 wt % water, e.g., less than 5 wt % or less than 1 wt %.

In some embodiments, the condensation reaction may achieve favorable conversion of acetic acid and favorable selectivity and productivity to acrylates. For purposes of the present invention, the term "conversion" refers to the amount of acetic acid in the feed that is converted to a compound other than acetic acid. Conversion is expressed as a percentage based on acetic acid in the feed. The conversion of acetic acid may be at least 10%, e.g., at least 20%, at least 40%, or at least 50%.

Selectivity, as it refers to the formation of acrylate product, is expressed as the ratio of the amount of carbon in the desired product(s) and the amount of carbon in the total products. This ratio may be multiplied by 100 to arrive at the selectivity. Preferably, the catalyst selectivity to acrylate products, e.g., acrylic acid and methyl acrylate, is at least 40 mol %, e.g., at least 50 mol %, at least 60 mol %, or at least 70 mol %. In some embodiments, the selectivity to acrylic acid is at least 30 mol %, e.g., at least 40 mol %, or at least 50 mol %; and/or the selectivity to methyl acrylate is at least 10 mol %, e.g., at least 15 mol %, or at least 20 mol %.

The terms "productivity" or "space time yield" as used herein, refers to the grams of a specified product, e.g., acrylate products, formed per hour during the condensation based on the liters of catalyst used. A productivity of at least 20 grams of acrylate product per liter catalyst per hour, e.g., at least 40 grams of acrylates per liter catalyst per hour or at least 100 grams of acrylates per liter catalyst per hour, is preferred. In terms of ranges, the productivity preferably is from 20 to 500 grams of acrylates per liter catalyst per hour, e.g., from 20 to 200 grams of acrylates per liter catalyst per hour or from 40 to 140 grams of acrylates per liter catalyst per hour.

In one embodiment, the inventive process yields at least 1,800 kg/hr of finished acrylic acid, e.g., at least 3,500 kg/hr, at least 18,000 kg/hr, or at least 37,000 kg/hr.

Preferred embodiments of the inventive process demonstrate a low selectivity to undesirable products, such as carbon monoxide and carbon dioxide. The selectivity to these undesirable products preferably is less than 29%, e.g., less than 25% or less than 15%. More preferably, these undesirable products are not detectable. Formation of alkanes, e.g., ethane, may be low, and ideally less than 2%, less than 1%, or less than 0.5% of the acetic acid passed over the catalyst is converted to alkanes, which have little value other than as fuel.

The alkanoic acid or ester thereof and alkylenating agent may be fed independently or after prior mixing to a reactor containing the catalyst. The reactor may be any suitable reactor or combination of reactors. Preferably, the reactor comprises a fixed bed reactor or a series of fixed bed reactors. In one embodiment, the reactor is a packed bed reactor or a series of packed bed reactors. In one embodiment, the reactor is a fixed bed reactor. Of course, other reactors such as a continuous stirred tank reactor or a fluidized bed reactor, may be employed.

In some embodiments, the alkanoic acid, e.g., acetic acid, and the alkylenating agent, e.g., formaldehyde, are fed to the reactor at a molar ratio of at least 0.10:1, e.g., at least 0.75:1 or at least 1:1. In terms of ranges the molar ratio of alkanoic acid to alkylenating agent may range from 0.10:1 to 10:1 or from 0.75:1 to 5:1. In some embodiments, the reaction of the alkanoic acid and the alkylenating agent is conducted with a stoichiometric excess of alkanoic acid. In these instances, acrylate selectivity may be improved. As an example the acrylate selectivity may be at least 10% higher than a selectivity achieved when the reaction is conducted with an excess of alkylenating agent, e.g., at least 20% higher or at least 30% higher. In other embodiments, the reaction of the alkanoic acid and the alkylenating agent is conducted with a stoichiometric excess of alkylenating agent.

The condensation reaction may be conducted at a temperature of at least 250° C., e.g., at least 300° C., or at least 350° C. In terms of ranges, the reaction temperature may range from 200° C. to 500° C., e.g., from 250° C. to 400° C., or from 250° C. to 350° C. Residence time in the reactor may range from 1 second to 200 seconds, e.g., from 1 second to 100 seconds. Reaction pressure is not particularly limited, and the reaction is typically performed near atmospheric pressure. In one embodiment, the reaction may be conducted at a pressure ranging from 0 kPa to 4100 kPa, e.g., from 3 kPa to 345 kPa, or from 6 to 103 kPa. The acetic acid conversion, in some embodiments, may vary depending upon the reaction temperature.

In one embodiment, the reaction is conducted at a gas hourly space velocity ("GHSV") greater than 600 hr$^{-1}$, e.g., greater than 1000 hr$^{-1}$ or greater than 2000 hr$^{-1}$. In one embodiment, the GHSV ranges from 600 hr$^{-1}$ to 10000 hr$^{-1}$, e.g., from 1000 hr$^{-1}$ to 8000 hr$^{-1}$ or from 1500 hr$^{-1}$ to 7500 hr$^{-1}$. As one particular example, when GHSV is at least 2000 hr$^{-1}$, the acrylate product STY may be at least 150 g/hr/liter.

Water may be present in the reactor in amounts up to 60 wt %, by weight of the reaction mixture, e.g., up to 50 wt % or up to 40 wt %. Water, however, is preferably reduced due to its negative effect on process rates and separation costs.

In one embodiment, an inert or reactive gas is supplied to the reactant stream. Examples of inert gases include, but are not limited to, nitrogen, helium, argon, and methane. Examples of reactive gases or vapors include, but are not limited to, oxygen, carbon oxides, sulfur oxides, and alkyl halides. When reactive gases such as oxygen are added to the reactor, these gases, in some embodiments, may be added in stages throughout the catalyst bed at desired levels as well as feeding with the other feed components at the beginning of the reactors. The addition of these additional components may improve reaction efficiencies.

In one embodiment, the unreacted components such as the alkanoic acid and formaldehyde as well as the inert or reactive gases that remain are recycled to the reactor after sufficient separation from the desired product.

When the desired product is an unsaturated ester made by reacting an ester of an alkanoic acid ester with formaldehyde, the alcohol corresponding to the ester may also be fed to the reactor either with or separately to the other components. For example, when methyl acrylate is desired, methanol may be fed to the reactor. The alcohol, amongst other effects, reduces the quantity of acids leaving the reactor. It is not necessary that the alcohol is added at the beginning of the reactor and it may for instance be added in the middle or near the back, in order to effect the conversion of acids such as propionic acid, methacrylic acid to their respective esters without depressing catalyst activity. In one embodiment, the alcohol may be added downstream of the reactor.

Catalyst Composition

Useful catalysts for the aldol condensation reaction include, for example, those disclosed in I & EC PRODUCT RESEARCH AND DEVELOPMENT, vol. 5, No. 1, March 1966, pages 50 to 53. This group of basic catalysts may comprise firstly zeolites (aluminosilicates) with anionic structural charge, on the inner and outer surfaces of which at least one cation type from the group of the alkali metal ions and alkaline earth metal ions is present (preferably Na$^+$, K$^+$, Ca$^{2+}$ and/or Mg$^{2+}$), in order to balance out (to neutralize) the negative structural charge. However, it also may comprise hydroxide applied to inert supports (e.g. amorphous silicon dioxide (silica gel)), from the group consisting of alkali metal hydroxides, alkaline earth metal hydroxides and aluminum hydroxide (preferably KOH, NaOH, Ca(OH)$_2$ and Mg(OH)$_2$).

Also suitable for the aldol condensation reaction are the acidic catalysts disclosed in EP-A 164614. These are catalysts may comprise: at least one oxide of at least one of the elements Si, Al, Ti, Zr, Cd, Sn, Ga, Y and La and/or zeolite, and at least one oxide selected from boron oxide and phosphorus oxide, and optionally one or more than one oxide of at least one of the elements V, Cr, Co, Ni, Mo and Pb and/or one or more than one heteropolyacid with at least one poly atom selected from V, Mo and W.

Preferred boron oxide is B$_2$O$_3$, and preferred phosphorus oxide is P$_2$O$_5$.

Preference is given to catalysts whose boron oxide content (calculated as B$_2$O$_3$ (based on the amount of B present)) is 1 to 50% by weight. In one embodiment, catalysts favorable in accordance with the invention are also those whose phosphorus oxide content (calculated as P$_2$O$_5$ (based on the amount of P present)) is 1 to 50% by weight. In one embodiment, useful aldol condensation catalysts for the process according to the invention also include those among the aforementioned catalysts whose total content of phosphorus oxide (calculated as P$_2$O$_5$) and of boron oxide (calculated as B$_2$O$_3$) is 1 to 50% by weight. The aforementioned contents of phosphorus oxide and/or boron oxide are preferably 5 to 30% by weight.

In addition, constituent a) is preferably at least one oxide of at least one of the elements Si, Al, Ti and Zr.

Particularly favorable in accordance with the invention are the combinations of titanium oxide as constituent a) and boron oxide or phosphorus oxide as constituent b), or silicon dioxide-aluminum oxide as constituent a) and boron oxide as constituent b), or aluminum oxide as constituent a) and boron oxide or phosphorus oxide as constituent b). When the catalysts detailed above additionally comprise a heteropolyacid, it preferably comprises at least one of the elements P, B and Si as a heteroatom. When the aforementioned catalysts comprise a constituent c), the amount thereof is normally 0.01 to 10 mmol per gram of catalyst and in many cases 0.03 to 5 mmol per gram of catalyst. It is favorable when the catalysts have, as constituent c), both at least one of the oxides and at least one of the heteropolyacids.

More preferably in accordance with the invention, the aldol condensation reaction zone is, however, charged with aldol condensation catalysts whose active material is a vanadium-phosphorus oxide and/or a vanadium-phosphorus oxide doped with elements other than vanadium and phosphorus (also referred to collectively in the literature as V—P—O catalysts).

Such catalysts have been described before in the literature and are recommended there especially as catalysts for the heterogeneously catalyzed partial gas phase oxidation of hydrocarbons having at least four carbon atoms (especially n-butane, n-butene and/or benzene) to maleic anhydride.

Surprisingly, these catalysts known from the references for aforementioned partial oxidations are suitable in principle as aldol condensation catalysts for charging the condensation reaction zone.

In one embodiment, the aldol condensation catalysts used in the process according to the invention may, for example, be selected from those disclosed in documents U.S. Pat. Nos. 5,275,996, 5,641,722, 5,137,860, 5,095,125, DE-69702728 T2, WO 2007/012620, WO 2010/072721, WO 2001/68245, U.S. Pat. No. 4,933,312, WO 2003/078310, Journal of Catalysis 107, pages 201-208 (1987), DE-A 102008040094, WO 97/12674, "Neuartige Vanadium (IV)-phosphate fur die Partialoxidation von kurzkettigen Kohlenwasserstoffen-Synthesen, Kristallstrukturen, Redox-Verhalten and katalytische Eigenschaften [Novel vanadium(IV) phosphates for the partial oxidation of short-chain hydrocarbon syntheses, crystal structures, redox behavior and catalytic properties], thesis by Ernst Benser, 2007, Rheinische Friedrichs-Wilhelms-Universitat Bonn", WO 2010/072723, "Untersuchung von V—P—O-Katalysatoren fur die partielle Oxidation von Propan zu Acrylsaure [Study of V—P—O catalysts for the partial oxidation of propane to acrylic acid], thesis by Thomas Quandt, 1999, Ruhr-Universitat Bochum", WO 2010/000720, WO 2008/152079, WO 2008/087116, DE-A 102008040093, DE-A 102005035978 and DE-A 102007005602, and the references acknowledged in these documents. In particular, this applies to all exemplary embodiments of the above prior art, especially those of WO 2007/012620.

The phosphorus/vanadium atomic ratio in the undoped or doped vanadium-phosphorus oxides is, advantageously in accordance with the invention, 0.9 to 2.0, preferably 0.9 to 1.5, more preferably 0.9 to 1.2 and most preferably 1.0 to 1.1. The arithmetic mean oxidation state of the vanadium therein is preferably +3.9 to +4.4 and more preferably 4.0 to 4.3. These active materials also advantageously have a specific BET surface area of $\geq 10$ m$^2$/g, e.g., $\geq 13$ m$^2$/g, or $\geq 15$ m$^2$/g, preferably of $\geq 10$ to 50 m$^2$/g and most preferably of $\geq 13$ to 40 m$^2$/g. They advantageously have a total pore volume of $\geq 0.1$ ml/g, preferably of 0.15 to 0.5 ml/g and most preferably of 0.15 to 0.4 ml/g. As already stated, the vanadium-phosphorus oxide active materials may be doped with promoter elements other than vanadium and phosphorus. Useful such promoter elements include the elements of groups 1 to 15 of the Periodic Table other than P and V. Doped vanadium-phosphorus oxides are disclosed, for example, by WO 97/12674, WO 95/26817, U.S. Pat. Nos. 5,137,860, 5,296,436, 5,158,923, 4,795,818 and WO 2007/012620.

Promoters preferred in accordance with the invention are the elements lithium, potassium, sodium, rubidium, cesium, thallium, molybdenum, zinc, hafnium, zirconium, titanium, chromium, manganese, nickel, copper, iron, boron, silicon, tin, niobium, cobalt and bismuth, among which preference is given not only to iron but especially to niobium, molybdenum, zinc and bismuth. The vanadium-phosphorus oxide active materials may comprise one or more promoter elements. The total content of promoters in the catalytic active material is, based on the weight thereof, generally not more than 5% by weight (the individual promoter element calculated in each case as the electrically uncharged oxide in which the promoter element has the same charge number (oxidation number) as in the active material).

Particularly useful active materials for aldol condensation catalysts for charging the condensation reaction zone may be multielement oxide active materials of the general formula I $$V_1P_bFe_cX^1_dX^2_eO_n \qquad (I),$$

in which the variables are each defined as follows:

$X^1$ is Mo, Bi, Co, Ni, Si, Zn, Hf, Zr, Ti, Cr, Mn, Cu, B, Sn and/or Nb, preferably Nb, Mo, Zn and/or Hf, $X^2$ is Li, K, Na, Rb, Cs and/or Tl, b is 0.9 to 2.0, preferably 0.9 to 1.5, more preferably 0.9 to 1.2 and most preferably 1.0 to 1.1, c ranges from 0.01 to 1, e.g, from 0.01 to 0.5 or from 0.01 to 0.1, d ranges from 0 to 0.1, e ranges from 0 to 0.1, and n is the stoichiometric coefficient of the element oxygen, which is determined by the stoichiometric coefficients of the non-oxygen elements and the charge numbers thereof in II.

Irrespective of the stoichiometric coefficients d, e and b, the stoichiometric coefficient c is, advantageously in accordance with the invention, in active materials of the general formula II, 0.005 to 0.1, preferably 0.005 to 0.05 and particularly advantageously, 0.005 to 0.02.

The aldol condensation catalysts may comprise the multimetal oxide active materials of the general formula I, for example, in pure, undiluted form, or diluted with an oxidic, essentially inert dilution material in the form of unsupported catalysts. Inert dilution materials suitable in accordance with the invention include, for example, finely divided aluminum oxide, silicon dioxide, aluminosilicates, zirconium dioxide, titanium dioxide or mixtures thereof. Undiluted unsupported catalysts are preferred in accordance with the invention. The unsupported catalysts may in principle be of any shape. Preferred shaped unsupported catalyst bodies are spheres, solid cylinders, hollow cylinders and trilobes, the longest dimension of which in all cases is advantageously 1 to 10 mm.

In the case of shaped unsupported catalyst bodies, the shaping may be advantageously performed with precursor powder that is calcined, e.g., after the shaping. The shaping is performed typically with addition of shaping assistants, for example graphite (lubricant) or mineral fibers (reinforcing aids). Suitable shaping processes are tableting and extrusion.

The external diameter of cylindrical unsupported catalysts is, in some embodiments, 3 to 10 mm, preferably 4 to 8 mm and in particular 5 to 7 mm. The height thereof is advantageously 1 to 10 mm, preferably 2 to 6 mm and in particular 3 to 5 mm. The same applies in the case of hollow cylinders. In addition, the internal diameter of the orifice running through from the top downward may be advantageously 1 to 8 mm, preferably 2 to 6 mm and most preferably 2 to 4 mm. A wall thickness of 1 to 3 mm may be used in the case of hollow cylinders. It will be appreciated that the doped or undoped vanadium-phosphorus oxide active materials can also be used in powder form, or as eggshell catalysts with an active material eggshell applied to the surface of inert shaped support bodies, as aldol condensation catalysts in the aldol condensation reaction zone.

In some embodiments, doped or undoped vanadium-phosphorus oxide active materials and unsupported catalysts manufactured therefrom can be produced as described in the reference documents, to which reference is made in this patent application.

For example, these documents include WO 2007/012620, WO 2010/07273, WO 2010/000720 and WO 2010/000764.

For example, the procedure may be as follows:
a) reaction of a pentavalent vanadium compound (e.g. $V_2O_5$) with an organic reducing solvent (e.g. isobutanol) in the presence of a pentavalent phosphorus compound (e.g. ortho- and/or pyrophosphoric acid) with heating to 75 to 205° C., preferably to 100 to 120° C.;
b) cooling of the reaction mixture to advantageously 40 to 90° C.;

c) optional addition of compounds comprising doping elements, for example iron(III) phosphate;
d) reheating to 75 to 205° C., preferably 100 to 120° C.;
e) isolation of the solid precursor material formed, comprising V, P, O and, for example, Fe (for example by filtering);
f) drying and/or thermal pretreatment of the precursor material (optionally until commencement of preforming by elimination of water from the precursor material);
g) addition of shaping aids, for example finely divided graphite or mineral fibers, and subsequent shaping to give the shaped unsupported catalyst precursor body by, for example, tableting;
h) subsequent thermal treatment of the shaped catalyst precursor bodies formed by heating in an atmosphere which comprises oxygen, nitrogen, noble gases, carbon dioxide, carbon monoxide and/or steam (for example as described in WO 2003/078310). The temperature of the thermal treatment generally exceeds 250° C., in many cases 300° C. or 350° C., but normally not 600° C., preferably not 550° C. and most preferably not 500° C.

For example, these documents include WO 2007/012620, WO 2010/07273, WO 2010/000720 and WO 2010/000764.

The space velocity of the catalyst charge on the condensation reaction zone of formaldehyde present in the reaction gas input mixture may, in accordance with the invention, be 1 to 100, preferably 2 to 50 and more preferably 3 to 30 or 4 to 10 l(STP)/l.h. The term "space velocity" is used as defined in DE-A 19927624. The particular fixed catalyst bed may, in some embodiment, consist only of catalysts comprising active material, in other embodiments the bed may consist of a mixture of catalysts comprising active material and inert shaped bodies.

In some embodiments wherein V—P—O catalysts are employed as aldol condensation catalysts in the reaction zone, formaldehyde conversion, based on a single pass of the reaction gas mixture through the reaction zone, is at least 95 mol %, usually at least 98 mol %. Selectivity of acrylic acid formation, based on formaldehyde converted, is generally 95 mol %, frequently 98 mol %.

Separation

As discussed above, the crude product stream is separated to yield an intermediate acrylate product stream. FIG. 1 is a flow diagram depicting the formation of the crude product stream and the separation thereof to obtain an intermediate acrylate product stream. Acrylate product system 100 comprises reaction zone 102 and alkylenating agent split zone 132. Reaction zone 102 comprises reactor 106, alkanoic acid feed, e.g., acetic acid feed, 108, alkylenating agent feed, e.g., formaldehyde feed 110, vaporizer 112 and reactor feed line 114.

Acetic acid and formaldehyde are fed to vaporizer 112 via lines 108 and 110, respectively, to create a vapor feed stream, which exits vaporizer 112 via line 114 and is directed to reactor 106. Optionally, oxygen and/or methanol feeds, not shown, are fed to vaporizer 112. In other embodiments, not shown, any or all of the components of the reaction mixture, e.g., acetic acid, formaldehyde, oxygen and/or methanol, may be fed directly to a reactor (not shown). In one embodiment, lines 108 and 110 (and, optionally, the oxygen and/or methanol feeds) may be combined and jointly fed to the vaporizer 112. The temperature of the vapor feed stream in line 114 is preferably from 200° C. to 600° C., e.g., from 250° C. to 500° C. or from 340° C. to 425° C. Alternatively, a vaporizer may not be employed and the reactants may be fed directly to reactor 106.

Any feed that is not vaporized may be removed from vaporizer 112 and may be recycled or discarded. In addition, although line 114 is shown as being directed to the upper half of reactor 106, line 114 may be directed to the middle or bottom of first reactor 106. Further modifications and additional components to reaction zone 102 and alkylenating agent split zone 132 are described below.

Reactor 106 contains the aldol condensation catalyst that is used in the reaction to form crude product stream, which is withdrawn, preferably continuously, from reactor 106 via line 116. Although FIG. 1 shows the crude product stream being withdrawn from the bottom of reactor 106, the crude product stream may be withdrawn from any portion of reactor 106. Exemplary composition ranges for the crude product stream are shown in Table 1 above.

In one embodiment, one or more guard beds (not shown) may be used upstream of the reactor to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens.

Figure 2:
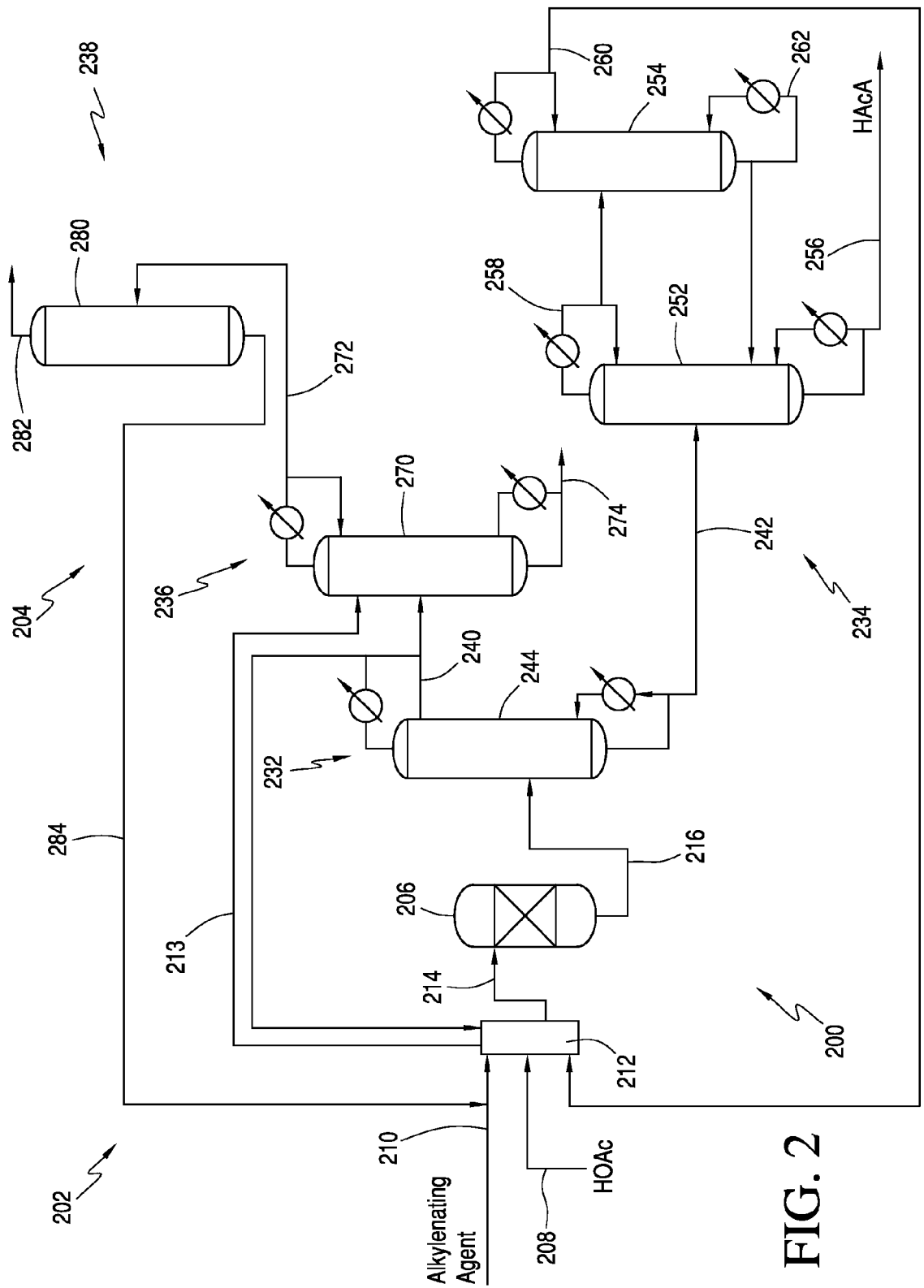
FIG. 2 is a schematic of an acrylic acid reaction/separation system in accordance with an embodiment of the present invention.
Figure 3:
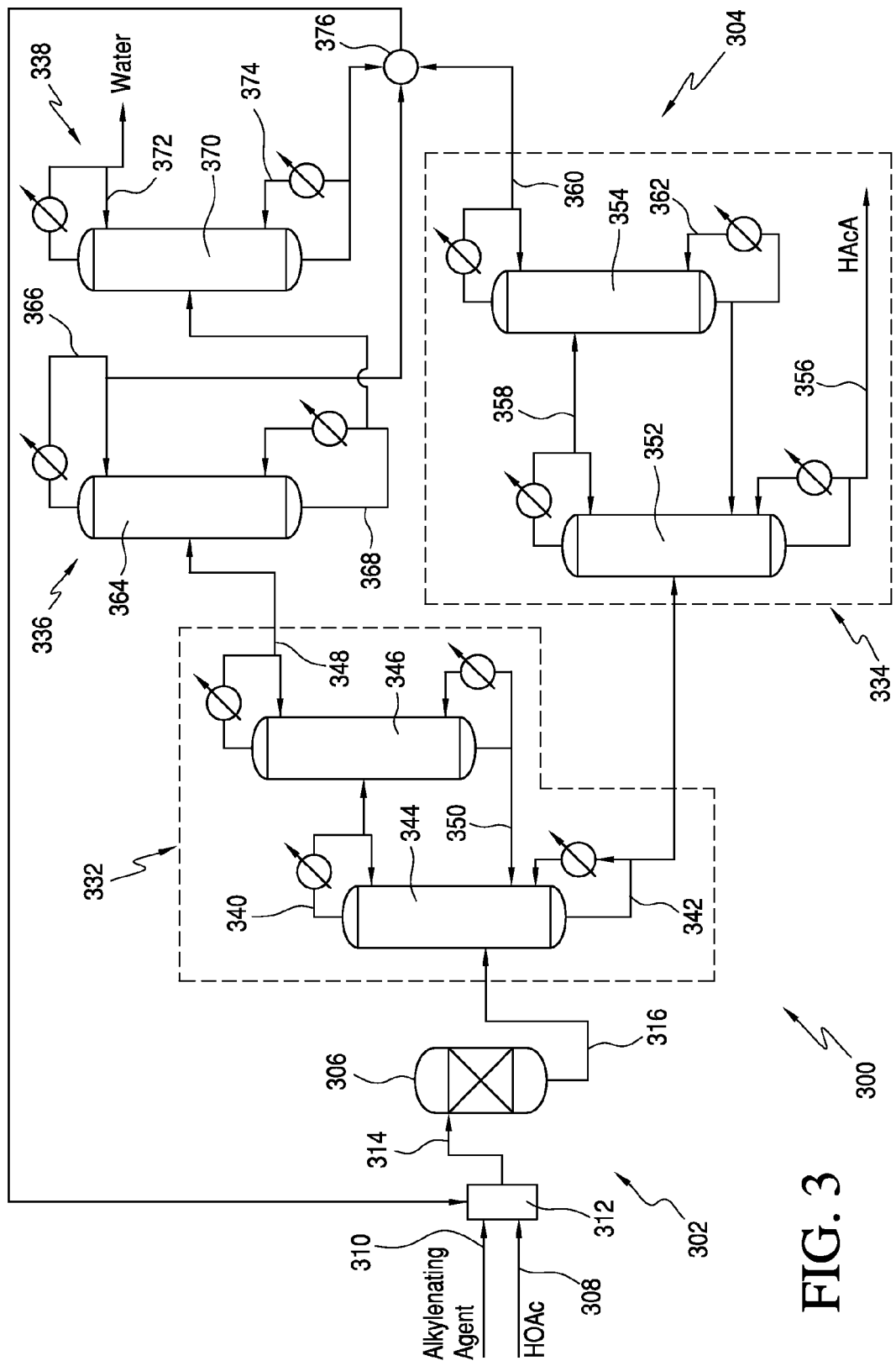
FIG. 3 is a schematic of an acrylic acid reaction/separation system in accordance with an embodiment of the present invention.

In one embodiment, the inventive process comprises the step of separating at least a portion of the condensation product gas mixture to form an alkylenating agent stream and an intermediate product stream. This separating step may be referred to as the "alkylenating agent split." The crude product stream in line 116 is fed to alkylenating agent split unit 132. Alkylenating agent split unit 132 may comprise one or more separation units, e.g., two or more or three or more. In one example, the alkylenating agent split unit contains multiple columns, as shown in FIGS. 2 and 3. Alkylenating agent split unit 132 separates the crude product stream into at least one intermediate acrylate product stream, which exits via line 118 and at least one alkylenating agent stream, which exits via line 120. Exemplary compositional ranges for the intermediate acrylate product stream are shown in Table 2 below. Components other than those listed in Table 2 may also be present in the intermediate acrylate product stream. Examples include methanol, methyl acetate, methyl acrylate, dimethyl ketone, carbon dioxide, carbon monoxide, oxygen, nitrogen, and acetone.

FIG. 2 shows an overview of a reaction/separation scheme in accordance with the present invention. Acrylate product system 200 comprises condensation reaction zone 202 and separation zone 204. Condensation reaction zone 202 comprises reactor 206, alkanoic acid feed, e.g., acetic acid feed 208, alkylenating agent feed, e.g., formaldehyde feed 210, vaporizer 212 and line 214. Reaction zone 202 and the components thereof function in a manner similar to reaction zone 102 of FIG. 1.

Condensation reaction zone 202 yields a condensation product gas mixture, which exits reaction zone 202 via line 216 and is directed to separation zone 204. The components of the condensation product gas mixture are discussed above.

As shown in FIG. 2, separation zone 204 contains multiple columns. Separation zone 204 comprises alkylenating agent split unit 232, acrylate product split unit 234, drying unit 236, and methanol removal unit 238.

Exemplary compositional ranges for the intermediate acrylate product stream are shown in Table 2. Components other than those listed in Table 2 may also be present in the intermediate acrylate product stream. Examples include methanol, methyl acetate, methyl acrylate, dimethyl ketone, carbon dioxide, carbon monoxide, oxygen, nitrogen, and acetone.

TABLE 2

INTERMEDIATE ACRYLATE PRODUCT STREAM COMPOSITION

|  | Conc. (wt. %) | Conc. (wt. %) | Conc. (wt. %) |
|---|---|---|---|
| Acrylic Acid | at least 5 | 5 to 99 | 35 to 65 |
| Acetic Acid | less than 95 | 5 to 90 | 20 to 60 |
| Water | less than 25 | 0.1 to 10 | 0.5 to 7 |
| Alkylenating Agent | <1 | <0.5 | <0.1 |
| Propionic Acid | <10 | 0.01 to 5 | 0.01 to 1 |

In one embodiment, the alkylenating agent stream comprises significant amounts of alkylenating agent(s). For example, the alkylenating agent stream may comprise at least 1 wt. % alkylenating agent(s), e.g., at least 5 wt. %, at least 10 wt. %, at least 15 wt. %, or at least 25 wt. %. In terms of ranges, the alkylenating stream may comprise from 1 wt. % to 75 wt. % alkylenating agent(s), e.g., from 3 to 50 wt. %, from 3 wt. % to 25 wt. %, or from 10 wt. % to 20 wt. %. In terms of upper limits, the alkylenating stream may comprise less than 75 wt. % alkylenating agent(s), e.g. less than 50 wt. % or less than 40 wt. %. In preferred embodiments, the alkylenating agent is formaldehyde.

In other embodiments, the intermediate acrylate product stream comprises higher amounts of alkylenating agent. For example, the intermediate acrylate product stream may comprise from 1 wt. % to 10 wt. % alkylenating agent, e.g., from 1 wt. % to 8 wt. % or from 2 wt. % to 5 wt. %. In one embodiment, the intermediate acrylate product stream comprises greater than 1 wt. % alkylenating agent, e.g., greater than 5 wt. % or greater than 10 wt. %.

Exemplary compositional ranges for the alkylenating agent stream are shown in Table 3. Components other than those listed in Table 3 may also be present in the purified alkylate product stream. Examples include methanol, methyl acetate, methyl acrylate, dimethyl ketone, carbon dioxide, carbon monoxide, oxygen, nitrogen, and acetone.

TABLE 3

ALKYLENATING AGENT STREAM COMPOSITION

|  | Conc. (wt. %) | Conc. (wt. %) | Conc. (wt. %) |
|---|---|---|---|
| Acrylic Acid | less than 15 | 0.01 to 10 | 0.1 to 5 |
| Acetic Acid | 10 to 65 | 20 to 65 | 25 to 55 |
| Water | 15 to 75 | 25 to 65 | 30 to 60 |
| Alkylenating Agent | at least 1 | 1 to 75 | 10 to 20 |
| Propionic Acid | <10 | 0.01 to 5 | 0.02 to 1 |

In other embodiments, the alkylenating stream comprises lower amounts of acetic acid. For example, the alkylenating agent stream may comprise less than 10 wt. % acetic acid, e.g., less than 5 wt. % or less than 1 wt. %.

As mentioned above, the condensation product gas mixture of the present invention comprises little, if any, furfural and/or acrolein. As such the derivative stream(s) of the condensation product gas mixture will comprise little, if any, furfural and/or acrolein. In one embodiment, the derivative stream(s), e.g., the streams of the separation zone, comprises less than less than 500 wppm acrolein, e.g., less than 100 wppm, less than 50 wppm, or less than 10 wppm. In one embodiment, the derivative stream(s) comprises less than less than 500 wppm furfural, e.g., less than 100 wppm, less than 50 wppm, or less than 10 wppm.

Separation zone 204 may also comprise a light ends removal unit (not shown). For example, the light ends removal unit may comprise a condenser and/or a flasher. The light ends removal unit may be configured either upstream of the alkylenating agent split unit. Depending on the configuration, the light ends removal unit removes light ends from the crude acrylate stream, the alkylenating stream, and/or the intermediate acrylate product stream. In one embodiment, when the light ends are removed, the remaining liquid phase comprises the acrylic acid, acetic acid, alkylenating agent, and/or water.

Alkylenating agent split unit 232 may comprise any suitable separation device or combination of separation devices. For example, alkylenating agent split unit 232 may comprise a column, e.g., a standard distillation column, an extractive distillation column and/or an azeotropic distillation column. In other embodiments, alkylenating agent split unit 232 comprises a precipitation unit, e.g., a crystallizer and/or a chiller. Preferably, alkylenating agent split unit 232 comprises a single distillation column.

In another embodiment, the alkylenating agent split is performed by contacting the condensation product gas mixture with a solvent that is immiscible with water. For example, alkylenating agent split unit 232 may comprise at least one liquid-liquid extraction column. In another embodiment, the alkylenating agent split is performed via azeotropic distillation, which employs an azeotropic agent. In these cases, the azeotropic agent may be selected from the group consisting of methyl isobutylketene, o-xylene, toluene, benzene, n-hexane, cyclohexane, p-xylene, and mixtures thereof. This listing is not exclusive and is not meant to limit the scope of the invention. In another embodiment, the alkylenating agent split is performed via a combination of distillations, e.g., standard distillation, and crystallization. Of course, other suitable separation devices may be employed either alone or in combination with the devices mentioned herein.

In FIG. 2, alkylenating agent split unit 232 comprises first column 244. The condensation product gas mixture in line 216 is directed to first column 244. First column 244 separates condensation product gas mixture to form a distillate in line 240 and a residue in line 242. The distillate may be refluxed and the residue may be boiled up as shown. Stream 240 comprises at least 1 wt % alkylenating agent. As such, stream 240 may be considered an alkylenating agent stream. The first column residue exits first column 244 in line 242 and comprises a significant portion of acrylate product. As such, stream 242 is an intermediate product stream. In one embodiment, at least a portion of stream 242 is directed to drying unit 236.

Exemplary compositional ranges for the distillate and residue of first column 244 are shown in Table 4. Components other than those listed in Table 4 may also be present in the residue and distillate.

TABLE 4

FIRST COLUMN

|  | Conc. (wt. %) | Conc. (wt. %) | Conc. (wt. %) |
|---|---|---|---|
| Distillate |  |  |  |
| Acrylic Acid | less than 5 | less than 3 | 0.05 to 1 |
| Acetic Acid | less than 10 | less than 5 | 0.5 to 3 |
| Water | 40 to 90 | 45 to 85 | 50 to 80 |
| Alkylenating Agent | at least 1 | 1 to 75 | 10 to 40 |
| Propionic Acid | less than 10 | less than 5 | less than 1 |
| Methanol | less than 5 | less than 1 | less than 0.5 |
| Residue |  |  |  |
| Acrylic Acid | 10 to 80 | 15 to 65 | 20 to 50 |
| Acetic Acid | 40 to 80 | 45 to 70 | 50 to 65 |

TABLE 4-continued

| FIRST COLUMN | | | |
|---|---|---|---|
| | Conc. (wt. %) | Conc. (wt. %) | Conc. (wt. %) |
| Water | 1 to 40 | 1 to 20 | 1 to 10 |
| Alkylenating Agent | at least 1 | 1 to 50 | 1 to 10 |
| Propionic Acid | less than 10 | less than 5 | less than 1 |

In one embodiment, the first distillate comprises smaller amounts of acetic acid, e.g., less than 25 wt %, less than 10 wt %, e.g., less than 5 wt % or less than 1 wt %. In one embodiment, the first residue comprises larger amounts of alkylenating agent.

In some embodiments, the intermediate acrylate product stream comprises higher amounts of alkylenating agent, e.g., greater than 1 wt % greater than 5 wt % or greater than 10 wt %.

For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

In one embodiment, polymerization inhibitors and/or anti-foam agents may be employed in the separation zone, e.g., in the units of the separation zone. The inhibitors may be used to reduce the potential for fouling caused by polymerization of acrylates. The anti-foam agents may be used to reduce potential for foaming in the various streams of the separation zone. The polymerization inhibitors and/or the anti-foam agents may be used at one or more locations in the separation zone.

In cases where any of alkylenating agent split unit 232 comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 300 kPa, e.g., from 10 kPa to 100 kPa or from 40 kPa to 80 kPa. In preferred embodiments, the pressure at which the column(s) are operated is kept at a low level e.g., less than 100 kPa, less than 80 kPa, or less than 60 kPa. In terms of lower limits, the column(s) may be operated at a pressures of at least 1 kPa, e.g., at least 20 kPa or at least 40 kPa. The surprising and unexpected benefits of these temperatures and pressure ranges and limits are discussed herein.

In one embodiment, the alkylenating agent split is achieved via one or more liquid-liquid extraction units. Preferably, the one or more liquid-liquid extraction units employ one or more extraction agents. Multiple liquid-liquid extraction units may be employed to achieve the alkylenating agent split. Any suitable liquid-liquid extraction devices used for multiple equilibrium stage separations may be used. Also, other separation devices, e.g., traditional columns, may be employed in conjunction with the liquid-liquid extraction unit(s).

In one embodiment (not shown), condensation product gas mixture is fed to a liquid-liquid extraction column where condensation product gas mixture is contacted with an extraction agent, e.g., an organic solvent. The liquid-liquid extraction column extracts the acids, e.g., acrylic acid and acetic acid, from condensation product gas mixture. An aqueous phase comprising water, alkylenating agent, and some acetic acid exits the liquid-liquid extraction unit. Small amounts of acrylic acid may also be present in the aqueous stream. The aqueous phase may be further treated and/or recycled. An organic phase comprising acrylic acid, acetic acid, and the extraction agent also exits the liquid-liquid extraction unit. The organic phase may also comprise water and formaldehyde. The acrylic acid may be separated from the organic phase and collected as product. The acetic acid may be separated then recycled and/or used elsewhere. The solvent may be recovered and recycled to the liquid-liquid extraction unit.

The inventive process further comprises the step of separating the intermediate acrylate product stream to form a finished acrylate product stream and a first finished acetic acid stream. The finished acrylate product stream comprises acrylate product(s) and the first finished acetic acid stream comprises acetic acid. The separation of the acrylate products from the intermediate product stream to form the finished acrylate product may be referred to as the "acrylate product split."

Returning to FIG. 2, intermediate product stream 242 exits alkylenating agent split unit 232 and is directed to acrylate product split unit 234 for further separation, e.g., to further separate the acrylate products therefrom. Acrylate product split unit 234 may comprise any suitable separation device or combination of separation devices. For example, acrylate product split unit 234 may comprise at least one column, e.g., a standard distillation column, an extractive distillation column and/or an azeotropic distillation column. In other embodiments, acrylate product split unit 234 comprises a precipitation unit, e.g., a crystallizer and/or a chiller. Preferably, acrylate product split unit 234 comprises two standard distillation columns as shown in FIG. 2. In another embodiment, acrylate product split unit 234 comprises a liquid-liquid extraction unit. Of course, other suitable separation devices may be employed either alone or in combination with the devices mentioned herein.

In FIG. 2, acrylate product split unit 234 comprises second column 252 and third column 254. Acrylate product split unit 234 receives at least a portion of purified acrylic product stream in line 242 and separates same into finished acrylate product stream 256 and at least one acetic acid-containing stream. As such, acrylate product split unit 234 may yield the finished acrylate product.

As shown in FIG. 2, at least a portion of purified acrylic product stream in line 242 is directed to second column 252. Second column 252 separates the purified acrylic product stream to form second distillate, e.g., line 258, and second residue, which is the finished acrylate product stream, e.g., line 256. The distillate may be refluxed and the residue may be boiled up as shown.

Stream 258 comprises acetic acid and some acrylic acid. The second column residue exits second column 252 in line 256 and comprises a significant portion of acrylate product. As such, stream 256 is a finished product stream. Exemplary compositional ranges for the distillate and residue of second column 252 are shown in Table 5. Components other than those listed in Table 5 may also be present in the residue and distillate.

TABLE 5

| SECOND COLUMN | | | |
|---|---|---|---|
| | Conc. (wt. %) | Conc. (wt. %) | Conc. (wt. %) |
| Distillate | | | |
| Acrylic Acid | 0.1 to 40 | 1 to 30 | 5 to 30 |
| Acetic Acid | 60 to 99 | 70 to 90 | 75 to 85 |

TABLE 5-continued

SECOND COLUMN

|  | Conc. (wt. %) | Conc. (wt. %) | Conc. (wt. %) |
|---|---|---|---|
| Water | 0.1 to 25 | 0.1 to 10 | 1 to 5 |
| Alkylenating Agent | 0.1 to 10 | 0.5 to 15 | 1 to 5 |
| Propionic Acid | less than 10 | 0.001 to 5 | 0.001 to 1 |
| Residue |  |  |  |
| Acrylic Acid | at least 85 | 85 to 99.9 | 95 to 99.5 |
| Acetic Acid | less than 15 | 0.1 to 10 | 0.1 to 5 |
| Water | less than 1 | less than 0.1 | less than 0.01 |
| Alkylenating Agent | less than 1 | less than 0.1 | less than 0.01 |
| Propionic Acid | less than 1 | less than 0.1 | less than 0.01 |

Returning to FIG. 2, at least a portion of stream 258 is directed to third column 254. Third column 254 separates the at least a portion of stream 258 into a distillate in line 260 and a residue in line 262. The distillate may be refluxed and the residue may be boiled up as shown. The distillate comprises a major portion of acetic acid. In one embodiment, at least a portion of line 260 is returned, either directly or indirectly, to reactor 206. The third column residue exits third column 254 in line 262 and comprises acetic acid and some acrylic acid. At least a portion of line 262 may be returned to second column 252 for further separation. In one embodiment, at least a portion of line 262 is returned, either directly or indirectly, to reactor 206. In another embodiment, at least a portion of the acetic acid-containing stream in either or both of lines 260 and 262 may be directed to an ethanol production system that utilizes the hydrogenation of acetic acid to form the ethanol. In another embodiment, at least a portion of the acetic acid-containing stream in either or both of lines 260 and 262 may be directed to a vinyl acetate system that utilizes the reaction of ethylene, acetic acid, and oxygen form the vinyl acetate. Exemplary compositional ranges for the distillate and residue of third column 254 are shown in Table 6. Components other than those listed in Table 6 may also be present in the residue and distillate.

TABLE 6

THIRD COLUMN

|  | Conc. (wt. %) | Conc. (wt. %) | Conc. (wt. %) |
|---|---|---|---|
| Distillate |  |  |  |
| Acrylic Acid | 0.01 to 10 | 0.05 to 5 | 0.1 to 1 |
| Acetic Acid | 50 to 99.9 | 70 to 99.5 | 80 to 99 |
| Water | 0.1 to 25 | 0.1 to 15 | 1 to 10 |
| Alkylenating Agent | 0.1 to 25 | 0.1 to 15 | 1 to 10 |
| Propionic Acid | less than 1 | less than 0.1 | less than 0.01 |
| Residue |  |  |  |
| Acrylic Acid | 5 to 50 | 15 to 40 | 20 to 35 |
| Acetic Acid | 50 to 95 | 60 to 80 | 65 to 75 |
| Water | 0.01 to 10 | 0.01 to 5 | 0.1 to 1 |
| Alkylenating Agent | less than 1 | 0.001 to 1 | 0.01 to 1 |
| Propionic Acid | less than 1 | less than 0.1 | less than 0.01 |

In cases where the acrylate product split unit comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 300 kPa, e.g., from 10 kPa to 100 kPa or from 40 kPa to 80 kPa. In preferred embodiments, the pressure at which the column(s) are operated is kept at a low level e.g., less than 50 kPa, less than 27 kPa, or less than 20 kPa. In terms of lower limits, the column(s) may be operated at a pressures of at least 1 kPa, e.g., at least 3 kPa or at least 5 kPa. Without being bound by theory, it has surprisingly and unexpectedly been found that be maintaining a low pressure in the columns of acrylate product split unit 234 may inhibit and/or eliminate polymerization of the acrylate products, e.g., acrylic acid, which may contribute to fouling of the column(s).

It has also been found that, surprisingly and unexpectedly, maintaining the temperature of acrylic acid-containing streams fed to acrylate product split unit 234 at temperatures below 140° C., e.g., below 130° C. or below 115° C., may inhibit and/or eliminate polymerization of acrylate products. In one embodiment, to maintain the liquid temperature at these temperatures, the pressure of the column(s) is maintained at or below the pressures mentioned above. In these cases, due to the lower pressures, the number of theoretical column trays is kept at a low level, e.g., less than 10, less than 8, less than 7, or less than 5. As such, it has surprisingly and unexpectedly been found that multiple columns having fewer trays inhibit and/or eliminate acrylate product polymerization. In contrast, a column having a higher amount of trays, e.g., more than 10 trays or more than 15 trays, would suffer from fouling due to the polymerization of the acrylate products. Thus, in a preferred embodiment, the acrylic acid split is performed in at least two, e.g., at least three, columns, each of which have less than 10 trays, e.g. less than 7 trays. These columns each may operate at the lower pressures discussed above.

Returning to FIG. 2, alkylenating agent stream 240 exits alkylenating agent split unit 232 and is directed to drying unit 236 for further separation, e.g., to further separate the water therefrom. The separation of the formaldehyde from the water may be referred to as dehydration. Drying unit 236 may comprise any suitable separation device or combination of separation devices. For example, drying unit 236 may comprise at least one column, e.g., a standard distillation column, an extractive distillation column and/or an azeotropic distillation column. In other embodiments, drying unit 236 comprises a dryer and/or a molecular sieve unit. In a preferred embodiment, drying unit 236 comprises a liquid-liquid extraction unit. In one embodiment, drying unit 236 comprises a standard distillation column as shown in FIG. 2. Of course, other suitable separation devices may be employed either alone or in combination with the devices mentioned herein.

In FIG. 2, drying unit 236 comprises fourth column 270. Drying unit 236 receives at least a portion of alkylenating agent stream in line 240 and separates same into a fourth distillate comprising water, formaldehyde, and methanol in line 272 and a fourth residue comprising mostly water in line 274. The distillate may be refluxed and the residue may be boiled up as shown. In one embodiment, at least a portion of line 272 is returned, either directly or indirectly, to reactor 206.

Exemplary compositional ranges for the distillate and residue of fourth column 270 are shown in Table 7. Components other than those listed in Table 7 may also be present in the residue and distillate.

TABLE 7

| FOURTH COLUMN | | | |
|---|---|---|---|
| | Conc. (wt. %) | Conc. (wt. %) | Conc. (wt. %) |
| Distillate | | | |
| Acrylic Acid | less than 1 | less than 0.1 | less than 0.01 |
| Acetic Acid | less than 2 | 0.01 to 1 | 0.01 to 1 |
| Water | 20 to 90 | 30 to 80 | 40 to 70 |
| Alkylenating Agent | 10 to 70 | 20 to 60 | 30 to 50 |
| Methanol | 0.01 to 15 | 0.1 to 10 | 1 to 5 |
| Residue | | | |
| Acrylic Acid | less than 1 | 0.001 to 1 | 0.01 to 1 |
| Acetic Acid | less than 15 | 0.1 to 10 | 0.1 to 5 |
| Water | at least 85 | 85 to 99.9 | 95 to 99.5 |
| Alkylenating Agent | less than 1 | 0.001 to 1 | 0.1 to 1 |
| Propionic Acid | less than 1 | less than 0.1 | less than 0.01 |

In cases where the drying unit comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 500 kPa, e.g., from 25 kPa to 400 kPa or from 100 kPa to 300 kPa.

Returning to FIG. 2, alkylenating agent stream 272 exits drying unit 236 and is directed to methanol removal unit 238 for further separation, e.g., to further separate the methanol therefrom. Methanol removal unit 238 may comprise any suitable separation device or combination of separation devices. For example, methanol removal unit 238 may comprise at least one column, e.g., a standard distillation column, an extractive distillation column and/or an azeotropic distillation column. In one embodiment, methanol removal unit 238 comprises a liquid-liquid extraction unit. In a preferred embodiment, methanol removal unit 238 comprises a standard distillation column as shown in FIG. 2. Of course, other suitable separation devices may be employed either alone or in combination with the devices mentioned herein.

In FIG. 2, methanol removal unit 238 comprises fifth column 280. Methanol removal unit 238 receives at least a portion of line 272 and separates same into a fifth distillate comprising methanol and water in line 282 and a fifth residue comprising water and formaldehyde in line 284. The distillate may be refluxed and the residue may be boiled up (not shown). In one embodiment, at least a portion of line 284 is returned, either directly or indirectly, to reactor 206. Fifth distillate 382 may be used to form additional formaldehyde.

Exemplary compositional ranges for the distillate and residue of fifth column 280 are shown in Table 8. Components other than those listed in Table 8 may also be present in the residue and distillate.

TABLE 8

| FIFTH COLUMN | | | |
|---|---|---|---|
| | Conc. (wt. %) | Conc. (wt. %) | Conc. (wt. %) |
| Distillate | | | |
| Acrylic Acid | less than 1 | less than 0.1 | less than 0.01 |
| Acetic Acid | less than 1 | less than 0.1 | less than 0.01 |
| Water | 20 to 60 | 30 to 50 | 35 to 45 |
| Alkylenating Agent | 0.1 to 25 | 0.5 to 20 | 1 to 15 |
| Methanol | 20 to 70 | 30 to 60 | 40 to 50 |
| Residue | | | |
| Acrylic Acid | less than 1 | less than 0.1 | less than 0.01 |
| Acetic Acid | less than 15 | 0.1 to 10 | 0.1 to 5 |
| Water | 40 to 80 | 50 to 70 | 55 to 65 |
| Alkylenating Agent | 20 to 60 | 30 to 50 | 35 to 45 |
| Methanol | less than 15 | 0.1 to 10 | 0.1 to 5 |

In cases where the methanol removal unit comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 500 kPa, e.g., from 25 kPa to 400 kPa or from 100 kPa to 300 kPa.

FIG. 3 shows an overview of a reaction/separation scheme in accordance with the present invention. Acrylate product system 300 comprises condensation reaction zone 302 and separation zone 304. Condensation reaction zone 302 comprises reactor 306, alkanoic acid feed, e.g., acetic acid feed 308, alkylenating agent feed, e.g., formaldehyde feed 310, vaporizer 312 and line 314. Reaction zone 302 and the components thereof function in a manner similar to reaction zone 102 of FIG. 1.

Condensation reaction zone 302 yields a condensation product gas mixture, which exits reaction zone 302 via line 316 and is directed to separation zone 304. The components of condensation product gas mixture are discussed above.

Reaction zone 302 yields a condensation product gas mixture, which exits reaction zone 302 via line 316 and is directed to separation zone 304. The components of condensation product gas mixture are discussed above. Separation zone 304 comprises alkylenating agent split unit 332, acrylate product split unit 334, acetic acid split unit 336, and drying unit 338. Separation zone 304 may also comprise a light ends removal unit (not shown). For example, the light ends removal unit may comprise a condenser and/or a flasher. The light ends removal unit may be configured either upstream of the alkylenating agent split unit. Depending on the configuration, the light ends removal unit removes light ends from the crude acrylate stream, the alkylenating stream, and/or the intermediate acrylate product stream. In one embodiment, when the light ends are removed, the remaining liquid phase comprises the acrylic acid, acetic acid, alkylenating agent, and/or water.

Alkylenating agent split unit 332 may comprise any suitable separation device or combination of separation devices. For example, alkylenating agent split unit 332 may comprise a column, e.g., a standard distillation column, an extractive distillation column and/or an azeotropic distillation column. In other embodiments, alkylenating agent split unit 332 comprises a precipitation unit, e.g., a crystallizer and/or a chiller. Preferably, alkylenating agent split unit 332 comprises two standard distillation columns. In another embodiment, the alkylenating agent split is performed by contacting the condensation product gas mixture with a solvent that is immiscible with water. For example alkylenating agent split unit 332 may comprise at least one liquid-liquid extraction columns. In another embodiment, the alkylenating agent split is performed via azeotropic distillation, which employs an azeotropic agent. In these cases, the azeotropic agent may be selected from the group consisting of methyl isobutylketene, o-xylene, toluene, benzene, n-hexane, cyclohexane, p-xylene, and mixtures thereof. This listing is not exclusive and is not meant to limit the scope of the invention. In another embodiment, the alkylenating agent split is performed via a combination of distillation, e.g., standard distillation, and crystallization. Of course, other suitable separation devices may be employed either alone or in combination with the devices mentioned herein.

In FIG. 3, alkylenating agent split unit 332 comprises sixth column 344 and seventh column 346. Alkylenating agent split unit 332 receives liquid acrylate stream in line 316 and separates same into at least one alkylenating agent stream, e.g., stream 348, and at least one intermediate product stream, e.g., stream 342. Alkylenating agent split unit 332 performs an alkylenating agent split, as discussed above.

In operation, as shown in FIG. 3, the condensation product gas mixture in line 316 is directed to sixth column 344. Sixth column 344 separates the condensation product gas mixture into a distillate in line 340 and a residue in line 342. The distillate may be refluxed and the residue may be boiled up as shown. Stream 340 comprises at least 1 wt. % alkylenating agent. As such, stream 340 may be considered an alkylenating agent stream. The sixth column residue exits sixth column 344 in line 342 and comprises a significant portion of acrylate product. As such, stream 342 is an intermediate product stream. Exemplary compositional ranges for the distillate and residue of sixth column 344 are shown in Table 9. Components other than those listed in Table 9 may also be present in the residue and distillate.

TABLE 9

SIXTH COLUMN

|  | Conc. (wt. %) | Conc. (wt. %) | Conc. (wt. %) |
|---|---|---|---|
| Distillate |  |  |  |
| Acrylic Acid | 0.1 to 20 | 1 to 10 | 1 to 5 |
| Acetic Acid | 25 to 65 | 35 to 55 | 40 to 50 |
| Water | 15 to 55 | 25 to 45 | 30 to 40 |
| Alkylenating Agent | at least 1 | 1 to 75 | 10 to 20 |
| Propionic Acid | <10 | 0.001 to 5 | 0.001 to 1 |
| Residue |  |  |  |
| Acrylic Acid | at least 5 | 5 to 99 | 35 to 65 |
| Acetic Acid | less than 95 | 5 to 90 | 20 to 60 |
| Water | less than 25 | 0.1 to 10 | 0.5 to 7 |
| Alkylenating Agent | <1 | <0.5 | <0.1 |
| Propionic Acid | <10 | 0.01 to 5 | 0.01 to 1 |

In one embodiments, the first distillate comprises smaller amounts of acetic acid, e.g., less than 25 wt. %, less than 10 wt. %, e.g., less than 5 wt. % or less than 1 wt. %. In one embodiment, the first residue comprises larger amounts of alkylenating agent, e.g., In other embodiments, the intermediate acrylate product stream comprises higher amounts of alkylenating agent, e.g., greater than 1 wt. % greater than 5 wt. % or greater than 10 wt. %.

In one embodiment, polymerization inhibitors and/or anti-foam agents may be employed in the separation zone, e.g., in the units of the separation zone. The inhibitors may be used to reduce the potential for fouling caused by polymerization of acrylates. The anti-foam agents may be used to reduce potential for foaming in the various streams of the separation zone. The polymerization inhibitors and/or the anti-foam agents may be used at one or more locations in the separation zone.

Returning to FIG. 3, at least a portion of stream 340 is directed to seventh column 346. Seventh column 346 separates the at least a portion of stream 340 into a distillate in line 348 and a residue in line 350. The distillate may be refluxed and the residue may be boiled up as shown. The distillate comprises at least 1 wt. % alkylenating agent. Stream 348, like stream 340, may be considered an alkylenating agent stream. The seventh column residue exits seventh column 346 in line 350 and comprises a significant portion of acetic acid. At least a portion of line 350 may be returned to sixth column 344 for further separation. In one embodiment, at least a portion of line 350 is returned, either directly or indirectly, to reactor 306. Exemplary compositional ranges for the distillate and residue of seventh column 346 are shown in Table 10. Components other than those listed in Table 10 may also be present in the residue and distillate.

TABLE 10

SEVENTH COLUMN

|  | Conc. (wt. %) | Conc. (wt. %) | Conc. (wt. %) |
|---|---|---|---|
| Distillate |  |  |  |
| Acrylic Acid | 0.01 to 10 | 0.05 to 5 | 0.1 to 0.5 |
| Acetic Acid | 10 to 50 | 20 to 40 | 25 to 35 |
| Water | 35 to 75 | 45 to 65 | 50 to 60 |
| Alkylenating Agent | at least 1 | 1 to 75 | 10 to 20 |
| Propionic Acid | 0.01 to 10 | 0.01 to 5 | 0.01 to 0.05 |
| Residue |  |  |  |
| Acrylic Acid | 0.1 to 25 | 0.05 to 15 | 1 to 10 |
| Acetic Acid | 40 to 80 | 50 to 70 | 55 to 65 |
| Water | 1 to 40 | 5 to 35 | 10 to 30 |
| Alkylenating Agent | at least 1 | 1 to 75 | 10 to 20 |
| Propionic Acid | <10 | 0.001 to 5 | 0.001 to 1 |

In cases where any of the alkylenating agent split unit comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 300 kPa, e.g., from 10 kPa to 100 kPa or from 40 kPa to 80 kPa. In preferred embodiments, the pressure at which the column(s) are operated is kept at a low level e.g., less than 100 kPa, less than 80 kPa, or less than 60 kPa. In terms of lower limits, the column(s) may be operated at a pressures of at least 1 kPa, e.g., at least 20 kPa or at least 40 kPa. Without being bound by theory, it is believed that alkylenating agents, e.g., formaldehyde, may not be sufficiently volatile at lower pressures. Thus, maintenance of the separation unit pressures, e.g., column pressures, at low levels surprisingly and unexpectedly provides for efficient separation operations. In addition, it has surprisingly and unexpectedly been found that maintenance of these low pressures may inhibit and/or eliminate polymerization of the acrylate products, e.g., acrylic acid, which may contribute to fouling of the column(s). Also, it has surprisingly and unexpectedly been found that by maintaining the temperature of the units, e.g., columns, at a low level (as discussed below), may inhibit and/or eliminate polymerization of the acrylate products.

In one embodiment, the alkylenating agent split is achieved via one or more liquid-liquid extraction units. Preferably, the one or more liquid-liquid extraction units employ one or more extraction agents. Multiple liquid-liquid extraction units may be employed to achieve the alkylenating agent split. Any suitable liquid-liquid extraction devices used for multiple equilibrium stage separations may be used. Also, other separation devices, e.g., traditional columns, may be employed in conjunction with the liquid-liquid extraction unit(s).

In one embodiment (not shown), the condensation product gas mixture is fed to a liquid-liquid extraction column where the condensation product gas mixture is contacted with an extraction agent, e.g., an organic solvent. The liquid-liquid extraction column extracts the acids, e.g., acrylic acid and acetic acid, from th condensation product gas mixture. An aqueous stage comprising water, alkylenating agent, and some acetic acid exits the liquid-liquid extraction unit. Small amounts of acylic acid may also be present in the aqueous stream. The aqueous phase may be further treated and/or recycled. An organic phase comprising acrylic acid, acetic acid, and the extraction agent also exits the liquid-liquid extraction unit. The organic phase may also comprise water and formaldehyde. The acrylic acid may be separated from the organic phase and collected as product. The acetic acid may be separated then recycled and/or used elsewhere. The solvent may be recovered and recycled to the liquid-liquid extraction unit.

The inventive process further comprises the step of separating the intermediate acrylate product stream to form a finished acrylate product stream and a first finished acetic acid stream. The finished acrylate product stream comprises acrylate product(s) and the first finished acetic acid stream comprises acetic acid. The separation of the acrylate products from the intermediate product stream to form the finished acrylate product may be referred to as the "acrylate product split."

Returning to FIG. 3, intermediate product stream 342 exits alkylenating agent split unit 332 and is directed to acrylate product split unit 334 for further separation, e.g., to further separate the acrylate products therefrom. Acrylate product split unit 334 may comprise any suitable separation device or combination of separation devices. For example, acrylate product split unit 334 may comprise at least one column, e.g., a standard distillation column, an extractive distillation column and/or an azeotropic distillation column. In other embodiments, acrylate product split unit 334 comprises a precipitation unit, e.g., a crystallizer and/or a chiller. Preferably, acrylate product split unit 334 comprises two standard distillation columns as shown in FIG. 3. In another embodiment, acrylate product split unit 334 comprises a liquid-liquid extraction unit. Of course, other suitable separation devices may be employed either alone or in combination with the devices mentioned herein.

In FIG. 3, acrylate product split unit 334 comprises eighth column 352 and ninth column 354. Acrylate product split unit 334 receives at least a portion of purified acrylic product stream in line 342 and separates same into finished acrylate product stream 356 and at least one acetic acid-containing stream. As such, acrylate product split unit 334 may yield the finished acrylate product.

As shown in FIG. 3, at least a portion of purified acrylic product stream in line 342 is directed to eighth column 352. Eighth column 352 separates the purified acrylic product stream to form eighth distillate, e.g., line 358, and eighth residue, which is the finished acrylate product stream, e.g., line 356. The distillate may be refluxed and the residue may be boiled up as shown.

Stream 358 comprises acetic acid and some acrylic acid. The eighth column residue exits eighth column 352 in line 356 and comprises a significant portion of acrylate product. As such, stream 356 is a finished product stream. Exemplary compositional ranges for the distillate and residue of eighth column 352 are shown in Table 11. Components other than those listed in Table 11 may also be present in the residue and distillate.

TABLE 11

EIGHTH COLUMN

| | Conc. (wt. %) | Conc. (wt. %) | Conc. (wt. %) |
|---|---|---|---|
| Distillate | | | |
| Acrylic Acid | 0.1 to 40 | 1 to 30 | 5 to 30 |
| Acetic Acid | 60 to 99 | 70 to 90 | 75 to 85 |
| Water | 0.1 to 25 | 0.1 to 10 | 1 to 5 |
| Alkylenating Agent | less than 1 | 0.001 to 1 | 0.1 to 1 |
| Propionic Acid | <10 | 0.001 to 5 | 0.001 to 1 |
| Residue | | | |
| Acrylic Acid | at least 85 | 85 to 99.9 | 95 to 99.5 |
| Acetic Acid | less than 15 | 0.1 to 10 | 0.1 to 5 |
| Water | less than 1 | less than 0.1 | less than 0.01 |
| Alkylenating Agent | less than 1 | 0.001 to 1 | 0.1 to 1 |
| Propionic Acid | 0.1 to 10 | 0.1 to 5 | 0.5 to 3 |

Returning to FIG. 3, at least a portion of stream 358 is directed to ninth column 354. Ninth column 354 separates the at least a portion of stream 358 into a distillate in line 360 and a residue in line 362. The distillate may be refluxed and the residue may be boiled up as shown. The distillate comprises a major portion of acetic acid. In one embodiment, at least a portion of line 360 is returned, either directly or indirectly, to reactor 306. The ninth column residue exits ninth column 354 in line 362 and comprises acetic acid and some acrylic acid. At least a portion of line 362 may be returned to eighth column 352 for further separation. In one embodiment, at least a portion of line 362 is returned, either directly or indirectly, to reactor 306. In another embodiment, at least a portion of the acetic acid-containing stream in either or both of lines 360 and 362 may be directed to an ethanol production system that utilizes the hydrogenation of acetic acid form the ethanol. In another embodiment, at least a portion of the acetic acid-containing stream in either or both of lines 360 and 362 may be directed to a vinyl acetate system that utilizes the reaction of ethylene, acetic acid, and oxygen form the vinyl acetate. Exemplary compositional ranges for the distillate and residue of ninth column 354 are shown in Table 12. Components other than those listed in Table 12 may also be present in the residue and distillate.

TABLE 12

NINTH COLUMN

| | Conc. (wt. %) | Conc. (wt. %) | Conc. (wt. %) |
|---|---|---|---|
| Distillate | | | |
| Acrylic Acid | 0.01 to 10 | 0.05 to 5 | 0.1 to 1 |
| Acetic Acid | 50 to 99.9 | 70 to 99.5 | 80 to 99 |
| Water | 0.1 to 25 | 0.1 to 15 | 1 to 10 |
| Alkylenating Agent | less than 10 | 0.001 to 5 | 0.01 to 5 |
| Propionic Acid | 0.0001 to 10 | 0.001 to 5 | 0.001 to 0.05 |
| Residue | | | |
| Acrylic Acid | 5 to 50 | 15 to 40 | 20 to 35 |
| Acetic Acid | 50 to 95 | 60 to 80 | 65 to 75 |
| Water | 0.01 to 10 | 0.01 to 5 | 0.1 to 1 |
| Alkylenating Agent | less than 1 | 0.001 to 1 | 0.1 to 1 |
| Propionic Acid | <10 | 0.001 to 5 | 0.001 to 1 |

In cases where the acrylate product split unit comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 300 kPa, e.g., from 10 kPa to 100 kPa or from 40 kPa to 80 kPa. In preferred embodiments, the pressure at which the column(s) are operated is kept at a low level e.g., less than 50 kPa, less than 27 kPa, or less than 20 kPa. In terms of lower limits, the column(s) may be operated at a pressures of at least 1 kPa, e.g., at least 3 kPa or at least 5 kPa. Without being bound by theory, it has surprisingly and unexpectedly been found that be maintaining a low pressure in the columns of acrylate product split unit 334 may inhibit and/or eliminate polymerization of the acrylate products, e.g., acrylic acid, which may contribute to fouling of the column(s).

It has also been found that, surprisingly and unexpectedly, maintaining the temperature of acrylic acid-containing streams fed to acrylate product split unit 334 at temperatures below 140° C., e.g., below 130° C. or below 115° C., may inhibit and/or eliminate polymerization of acrylate products. In one embodiment, to maintain the liquid temperature at these temperatures, the pressure of the column(s) is maintained at or below the pressures mentioned above. In these cases, due to the lower pressures, the number of theoretical column trays is kept at a low level, e.g., less than 10, less than 8, less than 7, or less than 5. As such, it has surprisingly and unexpectedly been found that multiple columns having fewer trays inhibit and/or eliminate acrylate product polymerization. In contrast, a column having a higher amount of trays, e.g., more than 10 trays or more than 15 trays, would suffer from fouling due to the polymerization of the acrylate products. Thus, in a preferred embodiment, the acrylic acid split is performed in at least two, e.g., at least three, columns, each of which have less than 10 trays, e.g. less than 7 trays. These columns each may operate at the lower pressures discussed above.

The inventive process further comprises the step of separating an alkylenating agent stream to form a purified alkylenating stream and a purified acetic acid stream. The purified alkylenating agent stream comprises a significant portion of alkylenating agent, and the purified acetic acid stream comprises acetic acid and water. The separation of the alkylenating agent from the acetic acid may be referred to as the "acetic acid split."

Returning to FIG. 3, alkylenating agent stream 348 exits alkylenating agent split unit 332 and is directed to acetic acid split unit 336 for further separation, e.g., to further separate the alkylenating agent and the acetic acid therefrom. Acetic acid split unit 336 may comprise any suitable separation device or combination of separation devices. For example, acetic acid split unit 336 may comprise at least one column, e.g., a standard distillation column, an extractive distillation column and/or an azeotropic distillation column. In other embodiments, acetic acid split unit 336 comprises a precipitation unit, e.g., a crystallizer and/or a chiller. Preferably, acetic acid split unit 336 comprises a standard distillation column as shown in FIG. 3. In another embodiment, acetic acid split unit 336 comprises a liquid-liquid extraction unit. Of course, other suitable separation devices may be employed either alone or in combination with the devices mentioned herein.

In FIG. 3, acetic acid split unit 336 comprises tenth column 364. Acetic acid split unit 336 receives at least a portion of alkylenating agent stream in line 348 and separates same into a tenth distillate comprising alkylenating agent in line 366, e.g., a purified alkylenating stream, and a tenth residue comprising acetic acid in line 368, e.g., a purified acetic acid stream. The distillate may be refluxed and the residue may be boiled up as shown. In one embodiment, at least a portion of line 366 and/or line 368 are returned, either directly or indirectly, to reactor 306. At least a portion of stream in line 368 may be further separated. In another embodiment, at least a portion of the acetic acid-containing stream in line 368 may be directed to an ethanol production system that utilizes the hydrogenation of acetic acid form the ethanol. In another embodiment, at least a portion of the acetic acid-containing stream in line 368 may be directed to a vinyl acetate system that utilizes the reaction of ethylene, acetic acid, and oxygen form the vinyl acetate.

The stream in line 366 comprises alkylenating agent and water. The stream in line 368 comprises acetic acid and water. Exemplary compositional ranges for the distillate and residue of tenth column 364 are shown in Table 13. Components other than those listed in Table 13 may also be present in the residue and distillate.

TABLE 13

| TENTH COLUMN | | | |
|---|---|---|---|
| | Conc. (wt. %) | Conc. (wt. %) | Conc. (wt. %) |
| Distillate | | | |
| Acrylic Acid | less than 1 | 0.001 to 5 | 0.001 to 1 |
| Acetic Acid | less than 1 | 0.001 to 5 | 0.001 to 1 |
| Water | 40 to 80 | 50 to 70 | 55 to 65 |
| Alkylenating Agent | 20 to 60 | 30 to 50 | 35 to 45 |
| Propionic Acid | less than 1 | 0.001 to 5 | 0.001 to 1 |
| Residue | | | |
| Acrylic Acid | less than 1 | 0.01 to 5 | 0.1 to 1 |
| Acetic Acid | 25 to 65 | 35 to 55 | 40 to 50 |
| Water | 35 to 75 | 45 to 65 | 50 to 60 |
| Alkylenating Agent | less than 1 | 0.01 to 5 | 0.1 to 1 |
| Propionic Acid | less than 1 | 0.01 to 5 | 0.02 to 1 |

In cases where the acetic acid split unit comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 500 kPa, e.g., from 25 kPa to 400 kPa or from 100 kPa to 300 kPa.

The inventive process further comprises the step of separating the purified acetic acid stream to form a second finished acetic acid stream and a water stream. The second finished acetic acid stream comprises a major portion of acetic acid, and the water stream comprises mostly water. The separation of the acetic from the water may be referred to as dehydration.

Returning to FIG. 3, tenth residue 368 exits acetic acid split unit 336 and is directed to drying unit 338 for further separation, e.g., to remove water from the acetic acid. Drying unit 338 may comprise any suitable separation device or combination of separation devices. For example, drying unit 338 may comprise at least one column, e.g., a standard distillation column, an extractive distillation column and/or an azeotropic distillation column. In other embodiments, drying unit 338 comprises a dryer and/or a molecular sieve unit. In a preferred embodiment, drying unit 338 comprises a liquid-liquid extraction unit. In one embodiment, drying unit 338 comprises a standard distillation column as shown in FIG. 3. Of course, other suitable separation devices may be employed either alone or in combination with the devices mentioned herein.

In FIG. 3, drying unit 338 comprises eleventh column 370. Drying unit 338 receives at least a portion of finished acetic acid stream in line 368 and separates same into an eleventh distillate comprising a major portion of water in line 372 and an eleventh residue comprising acetic acid and small amounts of water in line 374. The distillate may be refluxed and the residue may be boiled up as shown. In one embodiment, at least a portion of line 374 is returned, either directly or indirectly, to reactor 306. In another embodiment, at least a portion of the acetic acid-containing stream in line 374 may be directed to an ethanol production system that utilizes the hydrogenation of acetic acid form the ethanol. In another embodiment, at least a portion of the acetic acid-containing stream in line 374 may be directed to a vinyl acetate system that utilizes the reaction of ethylene, acetic acid, and oxygen form the vinyl acetate.

Exemplary compositional ranges for the distillate and residue of eleventh column 370 are shown in Table 14. Components other than those listed in Table 14 may also be present in the residue and distillate.

TABLE 14

ELEVENTH COLUMN

| | Conc. (wt. %) | Conc. (wt. %) | Conc. (wt. %) |
|---|---|---|---|
| Distillate | | | |
| Acrylic Acid | less than 1 | 0.001 to 5 | 0.001 to 1 |
| Acetic Acid | less than 1 | 0.01 to 5 | 0.01 to 1 |
| Water | 90 to 99.9 | 95 to 99.9 | 95 to 99.5 |
| Alkylenating Agent | less than 1 | 0.01 to 5 | 0.01 to 1 |
| Propionic Acid | less than 10 | 0.001 to 5 | 0.001 to 1 |
| Residue | | | |
| Acrylic Acid | less than 1 | 0.01 to 5 | 0.01 to 1 |
| Acetic Acid | 75 to 99.9 | 85 to 99.5 | 90 to 99.5 |
| Water | 25 to 65 | 35 to 55 | 40 to 50 |
| Alkylenating Agent | less than 1 | less than 0.001 | less than 0.0001 |
| Propionic Acid | less than 10 | 0.001 to 5 | 0.01 to 1 |

In cases where the drying unit comprises at least one column, the column(s) may be operated at suitable temperatures and pressures. In one embodiment, the temperature of the residue exiting the column(s) ranges from 90° C. to 130° C., e.g., from 95° C. to 120° C. or from 100° C. to 115° C. The temperature of the distillate exiting the column(s) preferably ranges from 60° C. to 90° C., e.g., from 65° C. to 85° C. or from 70° C. to 80° C. The pressure at which the column(s) are operated may range from 1 kPa to 500 kPa, e.g., from 25 kPa to 400 kPa or from 100 kPa to 300 kPa. FIG. 3 also shows tank 376, which collects at least one of the process streams prior to recycling same to reactor 306. Tank 376 is an optional feature. The various purge streams that may, alternatively, be recycled directly to reactor 306 without being collected in tank 376.

EXAMPLES

Example 1

Approximately 100 mL of isobutanol was heated to 90° C. in a flask with a mechanical stirrer and condenser. The desired amount of $V_2O_5$ (11.32 g) was slowly added as a powder to the well stirred hot isobutanol. Once the $V_2O_5$ was added, 85% $H_3PO_4$ (8.2 g) was slowly added with agitation to the hot mixture. Once the addition of $H_3PO_4$ was complete, the temperature of the mixture was increased to 100-108° C. and the mixture was stirred at this temperature for about 14 hours.

Ferric nitrate nonahydrate (53.5 g) was dissolved in deionized water. Ammonium hydroxide was added to form a precipitate. The precipitate was collected via centrifugation. Aqueous $H_3PO_4$ was added and stirred for 3.5 hours at 95° C. $H_2O_2$ (4 mL) was added to the white mixture and stirred for two hours. The mixture turned a light pink color. The $FePO_4$ was collected via centrifugation and washed with deionized water three times.

The desired amount of $FePO_4$ was added to the $V_2O_5$—$H_3PO_4$-iBuOH mixture and the mixture was stirred at reflux for one hour. The mixture was allowed to cool and the catalyst in solid form was isolated via filtration or centrifugation. The solid was washed once with EtOH and twice more with deionized water. The solid was dried overnight at 120° C. with flowing air. The final VFePO solid was ground to form a mixture and then calcined using the following temperature profile:

i) heating from room temperature to 160° C. at a rate of 10° C. per minute;
ii) heating at 160° C. for 2 hours;
iii) heating from 160° C. to 250° C. at a rate of 3° C. per minute;
iv) heating at 250° C. for 2 hours;
v) heating from 250° C. to 300° C. at a rate of 3° C. per minute;
vi) heating at 300° C. for 6 hours;
vii) heating from 300° C. to 450° C. at a rate of 3° C. per minute; and
viii) heating at 450° C. for 6 hours.

Example 2

Catalyst compositions were prepared using an iron salt ferric nitrate nonahydrate and a vanadium precursor, e.g., $NH_4VO_3$. Colloidal silica, deionized water, and ethylene glycol were combined and mixed. An organic acid, e.g. citric acid, was added to the mixture and the mixture was heated to 50° C. A calculated amount of $NH_4VO_3$ was added to the mixture and the resulting solution was heated to 80° C. with stirring. An amount of a iron nitrate dissolved in deionized water was added to the heated mixture. A 2 wt % solution of methyl cellulose was added to the bismuth salt/vanadium salt/vanadium precursor solution and stirred at 80 C. A calculated amount of phosphoric acid (85%) was added and the resulting solution was stirred. The final mixture was then evaporated to dryness overnight in a drying oven at 120° C., ground and calcined using the temperature profile discussed in Example 1.

Table 15 shows the catalyst composition for Catalysts 1-6, prepared via the method of Example

TABLE 15

| Catalyst | Catalyst Formula | Preparation Details | V:Fe Ratio | wt % V | wt % Fe | wt % P | wt % O |
|---|---|---|---|---|---|---|---|
| 1 | $VFe_{0.016}P_{1.05}O_{4.7}$ | Isobutanol + 0.016 $FePO_4$ | 63 | 32 | 0.6 | 20 | 47 |
| 2 | $VFe_{0.11}P_{1.144}O_5$ | Isobutanol + 0.11 $FePO_3$ | 9.1 | 30 | 3.6 | 21 | 46 |
| 3 | $VFe_{0.05}P_{1.534}O_{6.4}$ | Isobutanol + 0.5 $FePO_3$ | 2.0 | 22 | 12.2 | 21 | 45 |
| 4 | $V_{10}Fe_{0.16}P_{11.7}O_{51}$ | Citric acid- 2.5% EG $SiO_2$-10% MC | 63 | 29 | 0.5 | 21 | 57 |
| 5 | $V_{10}Fe_{0.1}P_{11.6}O_{51}$ | Citric acid- 2.5% EG $SiO_2$-10% MC | 100 | 30 | 0.3 | 21 | 57 |
| 6 | $V_{10}Fe_{0.16}P_{11.7}O_{51}$ | Citric acid- 5.8% EG $SiO_2$-10% MC | 63 | 28 | 0.5 | 20 | 45 |

Example 3

A reaction feed comprising acetic acid, formaldehyde, methanol, water, oxygen, and nitrogen was passed through a fixed bed reactor comprising Catalysts 1-6 and Comparative Catalyst A, a commercially available V—P—O catalyst. The reactions were conducted at a reactor temperature of 375° C. and a GHSV of 2000 $Hr^{-1}$, Total organics were 32 mole %; the acetic acid-to-formaldehyde ratio was 1.5. The feed comprised 4.8 mol % $O_2$, 7.2 mol % water, and 56 mole % $N_2$. Acrylic acid and methyl acrylate (collectively, "acrylate product") were produced. Acetic acid conversion, acrylate selectivity, acrylate yield, and acrylate space time yield were measured for Catalysts 1-6 and Comparative Catalyst A at various time points of the reaction. The results are shown in Table 16.

TABLE 16

| Catalyst | Runtime (h) | HOAc Conv. (%) | Acrylate Selectivity (%) | Acrylate Yield (%) | Acrylate STY (g/hr/L) |
|---|---|---|---|---|---|
| Acrylate Production; Catalysts 1-6 | | | | | |
| 1 | 0.5 | 36 | 88 | 32 | 421 |
|  | 1.2 | 36 | 88 | 32 | 418 |
|  | 1.9 | 36 | 88 | 32 | 414 |
|  | 19.0 | 40 | 85 | 34 | 451 |
|  | 20.2 | 40 | 86 | 34 | 453 |
|  | 21.5 | 39 | 86 | 34 | 444 |
|  | 22.6 | 39 | 87 | 33 | 438 |
|  | 24.0 | 37 | 87 | 32 | 424 |
|  | 42.7 | 40 | 85 | 34 | 451 |
|  | 45.0 | 40 | 87 | 35 | 454 |
|  | Avg. | 38 | 87 | 33 | 437 |
| 2 | 0.6 | 35 | 90 | 32 | 417 |
|  | 1.8 | 35 | 88 | 31 | 410 |
|  | 2.9 | 35 | 88 | 31 | 410 |
|  | 4.1 | 36 | 88 | 32 | 417 |
|  | 5.3 | 36 | 88 | 32 | 415 |
|  | 53.0 | 38 | 86 | 33 | 427 |
|  | Avg. | 36 | 88 | 32 | 416 |
| 3 | 0.6 | 32 | 89 | 29 | 375 |
|  | 1.8 | 33 | 88 | 29 | 374 |
|  | 2.9 | 33 | 88 | 29 | 375 |
|  | 4.1 | 33 | 88 | 29 | 381 |
|  | 5.1 | 33 | 88 | 29 | 380 |
|  | 53.0 | 37 | 84 | 31 | 402 |
|  | 54.1 | 37 | 86 | 32 | 418 |
|  | Avg. | 34 | 87 | 30 | 386 |
| 4 | 0.6 | 40 | 79 | 32 | 410 |
|  | 1.8 | 40 | 79 | 32 | 405 |
|  | 3.3 | 40 | 79 | 31 | 404 |
|  | 23.5 | 38 | 80 | 30 | 390 |
|  | 24.8 | 38 | 79 | 30 | 385 |
|  | Avg. | 39 | 79 | 31 | 401 |
| 5 | 1.4 | 41 | 86 | 35 | 456 |
|  | 2.3 | 40 | 85 | 34 | 439 |
|  | 3.3 | 40 | 84 | 33 | 434 |
|  | 5.5 | 38 | 90 | 34 | 442 |
|  | Avg. | 40 | 86 | 34 | 443 |
| 6 | 0.6 | 43 | 79 | 34 | 444 |
|  | 0.7 | 44 | 77 | 34 | 447 |
| Acrylate Production; Comparative Catalyst A | | | | | |
|  | 1.6 | 42 | 78 | 33 | 436 |
|  | 1.7 | 44 | 78 | 34 | 449 |
|  | 2.7 | 43 | 78 | 34 | 447 |
|  | 2.8 | 42 | 79 | 33 | 437 |
|  | 3.7 | 43 | 77 | 34 | 443 |
|  | 4.2 | 42 | 79 | 33 | 438 |
|  | 4.6 | 42 | 78 | 33 | 436 |
|  | 5.7 | 43 | 78 | 33 | 440 |
|  | Avg. | 43 | 78 | 34 | 442 |
| Comp. A | 0.8 | 27 | 85 | 23 | 304 |
|  | 1.7 | 24 | 94 | 22 | 289 |
|  | 2.7 | 23 | 95 | 22 | 280 |
|  | 3.9 | 22 | 97 | 21 | 277 |
|  | Avg. | 24 | 93 | 22 | 287 |

Acetic acid conversion, acrylate selectivity, acrylate yield, and acrylate space time yield were measured for Catalysts 1-6 and Comparative Catalyst A at various time points of the reaction. Catalysts 1-6 contain vanadium, iron, phosphorus, and oxygen, unexpectedly outperform Comparative Catalyst A. As shown in Table 16, Catalysts 1-6 show better acetic acid conversions, acrylate yield, and acrylate STY than Comparative Catalyst A.

Furthermore, surprisingly Catalysts 1-6 maintained steady acetic acid conversion, acrylate selectivity, acrylate yield, and acrylate STY over long time periods, i.e., Catalysts 1-6 showed little if any catalyst deactivation.

For example, for Catalyst 1, acetic acid conversion varied by only 4% (between 36% and 40%) over 45 hours and acrylate selectivity varied by only 3% over 45 hours. Catalyst 2 acetic acid conversion varied by only 3% over 53 hours and acrylate selectivity varied by only 4% over 53 hours. Catalyst 3 acetic acid conversion varied by only 5% over 54.1 hours and acrylate selectivity varied by only 5% over 54.1 hours. Catalyst 4 acetic acid conversion varied by only 2% over 24.8 hours and acrylate selectivity varied by only 1% over 24.8 hours. Catalyst 5 acetic acid conversion varied by only 3% over 5.5 hours and acrylate selectivity varied by only 6% over 5.7 hours. Catalyst 6 acetic acid conversion varied by only 2% over 5.5 hours and acrylate selectivity varied by only 2% over 5.7 hours.

In comparison, for Comparative Catalyst A, acetic acid conversion varied by 5% after only 3.9 hours; acrylate selectivity varied by 12% after only 3.9 hours. Of course, these differences are only exemplary and are not meant to exclude other improvements over the conventional catalyst.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing an acrylate product, the process comprising the steps of:
    contacting an alkanoic acid or an ester thereof and an alkylenating agent over an aldol condensation catalyst in a reaction zone and under conditions effective to produce a crude product stream comprising acrylate product and alkylenating agent, and
    separating at least a portion of the crude product stream to form an alkylenating agent stream comprising at least 1 wt % alkylenating agent and an intermediate product stream comprising acrylate product
    wherein the aldol condensation catalyst comprises a multi-element oxide active material of the general formula:

$V_1P_bFe_cX^1_dX^2_eO_n$ wherein:
    $X^1$ is Mo, Bi, Co, Ni, Si, Zn, Hf, Zr, Ti, Cr, Mn, Cu, B, Sn and/or Nb,
    $X^2$ is Li, K, Na, Rb, Cs and/or Tl,
    b ranges from 0.9 to 2.0
    c ranges from 0.01 to 1,
    d ranges from 0 to 0.1,
    e ranges from 0 to 0.1, and
    n is the stoichiometric coefficient of the element oxygen as determined by the stoichiometric coefficients of the non-oxygen elements and the charge numbers thereof.

2. The process of claim 1, wherein a molar ratio of alkanoic acid to alkylenating agent is at least 0.50:1.

3. The process of claim 1, wherein c ranges from 0.005 to 0.1.

4. The process of claim 1, wherein the aldol condensation catalyst is diluted with inert dilution materials selected from the group consisting of finely divided aluminum oxide, silicon dioxide, aluminosilicates, zirconium dioxide, titanium dioxide and mixtures thereof.

5. The process of claim 1, wherein the intermediate acrylate product stream further comprises less than 25 wt % water and less than 95 wt % acetic acid.

6. The process of claim 1, wherein the intermediate acrylate product stream comprises at least one of acrylic acid, acrylate, and acetic acid.

7. The process of claim 1, further comprising the step of:
    separating the intermediate acrylate product stream to form a finished acrylate product stream comprising acrylate products and a first finished acetic acid stream comprising acetic acid.

8. The process of claim 7, wherein the separating of the intermediate acrylate product step is performed in at least one column.

9. The process of claim 8, wherein the separating of the intermediate acrylate product step is performed in at least two columns, each of which has less than 10 theoretical trays.

10. The process of claim 9, wherein at least a portion of the first finished acetic acid stream is recycled to the reaction zone.

11. The process of claim 1, further comprising the step of:
    separating the alkylenating agent stream to form a purified alkylenating stream comprising at least 1 wt % alkylenating agent and a purified acetic acid stream comprising acetic acid and water.

12. The process of claim 11, wherein at least a portion of the purified alkylenating agent stream is recycled to the reaction zone.

13. The process of claim 11, further comprising the step of:
    separating the purified acetic acid stream to form a second finished acetic acid stream and a water stream.

14. The process of claim 13, wherein the separating of the purified acetic acid stream step is performed in at least one column.

15. The process of claim 13, wherein at least a portion of the second finished acetic acid stream is recycled to the reaction zone.

16. The process of claim 1, further comprising the step of:
    dehydrating the alkylenating agent stream to form a first purified alkylenating stream comprising methanol and at least 1 wt % alkylenating agent and a water stream.

17. The process of claim 16, wherein at least a portion of the first purified alkylenating stream is recycled to the reaction zone.

18. The process of claim 16, further comprising the step of:
    separating the first purified alkylenating agent stream to form a methanol stream and a second purified alkylenating agent stream comprising alkylenating agent.

19. The process of claim 18, wherein the second purified alkylenating agent stream is recycled to the reaction zone.

20. The process of claim 1, wherein the crude product stream comprises:
    acrylate product comprising from 5 wt % to 50 wt % acrylic acid,
    from 0.5 wt % to 50 wt % alkylenating agent comprising formaldehyde and/or precursors thereof,
    from 5 wt % to 50 wt % acetic acid, and
    from 1 wt % to 60 wt % water.

* * * * *